(12) United States Patent
Ek et al.

(10) Patent No.: US 12,661,232 B2
(45) Date of Patent: Jun. 23, 2026

(54) SYSTEM AND METHOD FOR REPAIRING ARTICULAR SURFACES

(71) Applicant: Arthrosurface Incorporated, Franklin, MA (US)

(72) Inventors: Steven W. Ek, Durham, NH (US); Anthony Miniaci, Bentleyville, OH (US); Timothy Brightman, Franklin, MA (US)

(73) Assignee: Arthrosurface Incorporated, West Bridgewater, MA (US)

( * ) Notice: Subject to any disclaimer, the term of this patent is extended or adjusted under 35 U.S.C. 154(b) by 633 days.

(21) Appl. No.: 18/165,104

(22) Filed: Feb. 6, 2023

(65) Prior Publication Data

US 2023/0255781 A1 Aug. 17, 2023

Related U.S. Application Data

(63) Continuation of application No. 16/854,260, filed on Apr. 21, 2020, now Pat. No. 11,607,319, which is a continuation of application No. 15/388,808, filed on Dec. 22, 2016, now Pat. No. 10,624,748, which is a
(Continued)

(51) Int. Cl.
| | |
|---|---|
| *A61F 2/30* | (2006.01) |
| *A61F 2/40* | (2006.01) |
| *A61F 2/46* | (2006.01) |

(52) U.S. Cl.
CPC ........ *A61F 2/4014* (2013.01); *A61F 2/30749* (2013.01); *A61F 2/4637* (2013.01); *A61F 2002/30143* (2013.01); *A61F 2002/30242* (2013.01); *A61F 2002/30245* (2013.01); *A61F 2002/30331* (2013.01); *A61F 2002/30406*

(2013.01); *A61F 2002/30461* (2013.01); *A61F 2002/30462* (2013.01); *A61F 2002/30518* (2013.01); *A61F 2002/30593* (2013.01); *A61F 2002/4037* (2013.01); *A61F 2310/00017* (2013.01); *A61F 2310/00023* (2013.01); *A61F 2310/00029* (2013.01)

(58) Field of Classification Search
None
See application file for complete search history.

(56) References Cited

U.S. PATENT DOCUMENTS

| | | | | | |
|---|---|---|---|---|---|
| 5,645,589 | A | * | 7/1997 | Li | F16B 13/08 |
| | | | | | 411/80 |
| 2004/0148030 | A1 | * | 7/2004 | Ek | A61B 90/06 |
| | | | | | 623/20.14 |
| 2014/0277558 | A1 | * | 9/2014 | Kurtz | A61F 2/30749 |
| | | | | | 623/22.36 |

* cited by examiner

*Primary Examiner* — Megan Y Wolf
(74) *Attorney, Agent, or Firm* — Secant IP, P.L.L.C.

(57) ABSTRACT

A joint replacement system for repairing an articular surface of a first bone of a joint includes an anchor portion and an implant portion. The anchor portion includes an anchor to be secured to the bone, and an anchor fixation head including a bone-facing surface (BFS) extending radially outward from the anchor and an implant facing surface (IFS) extending from a periphery of the BFS. The implant portion is formed from a material (e.g., CoCr) more dense than the material of the anchor portion (e.g., Ti) and includes a fixation cavity to receive at least a portion of the anchor fixation head (AFH), the fixation cavity includes an anchor facing surface (AFS) configured to form a frictional connection with the IFS, and a load bearing surface having a contour for articulating against a cooperating articulating surface of a second bone of the joint.

18 Claims, 23 Drawing Sheets

Related U.S. Application Data continuation-in-part of application No. 14/640,774, filed on Mar. 6, 2015, now Pat. No. 9,962,265.

(60) Provisional application No. 61/950,762, filed on Mar. 10, 2014, provisional application No. 61/949,824, filed on Mar. 7, 2014, provisional application No. 61/949,789, filed on Mar. 7, 2014, provisional application No. 61/949,774, filed on Mar. 7, 2014.

10

10

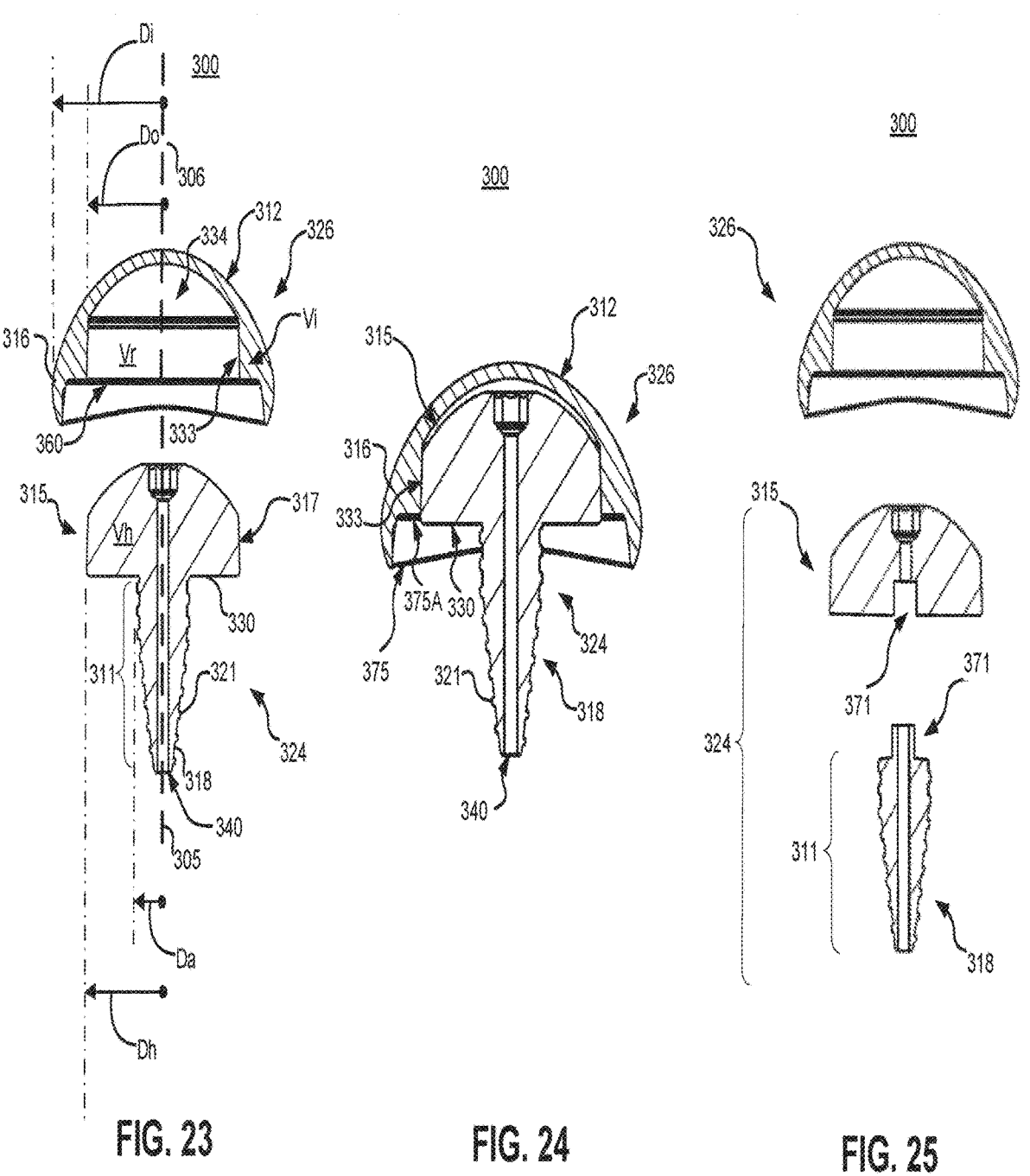
FIG. 23        FIG. 24        FIG. 25

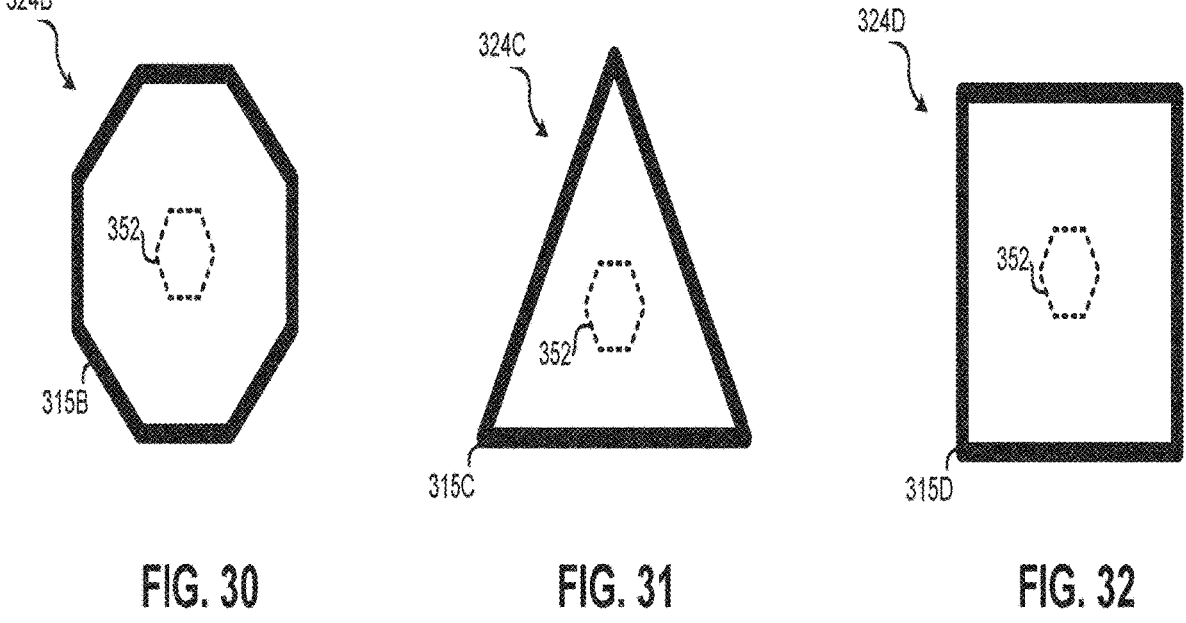
FIG. 30                    FIG. 31                    FIG. 32

SYSTEM AND METHOD FOR REPAIRING ARTICULAR SURFACES

CROSS REFERENCE TO RELATED APPLICATIONS

This application is a continuation U.S. patent application Ser. No. 16/854,260, filed Apr. 21, 2020, which is a continuation of U.S. patent application Ser. No. 15/388,808 (now U.S. Pat. No. 10,624,748), filed Dec. 22, 2016, which is a continuation-in-part of U.S. patent application Ser. No. 14/640,774 (now U.S. Pat. No. 9,962,265), filed Mar. 6, 2015, which claims the benefit of U.S. Provisional Application Ser. No. 61/949,774, filed Mar. 7, 2014; U.S. Provisional Application Ser. No. 61/949,789, filed Mar. 7, 2014; U.S. Provisional Application Ser. No. 61/949,824, filed Mar. 7, 2014; and U.S. Provisional Application Ser. No. 61/950, 762, filed Mar. 10, 2014, the entire disclosures of which are fully incorporated herein by reference.

FIELD

The present disclosure relates to delivery systems for bone implants, and more particularly, to delivery systems for articular surface implants.

BACKGROUND

Articular cartilage, found at the ends of articulating bone in the body, is typically composed of hyaline cartilage, which has many unique properties that allow it to function effectively as a smooth and lubricious load-bearing surface. When injured, however, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspects of native hyaline cartilage and tends to be far less durable.

In some cases, it may be necessary or desirable to repair the damaged articular cartilage using an implant. One method of installing an implant involves applying a blunt force, e.g., a hammer/mallet or the like, to the implant. Unfortunately, some of the blunt force is transmitted from the implant into the surrounding bone and/or tissue and can cause damage to the bone/tissue. This is particularly problematic in small bones (such as, but not limited to, bones in the hand and/or foot) as well as patients who suffer from reduced bone mass and density that can lead to fracture (such as, but not limited to, osteoporosis or the like).

BRIEF DESCRIPTION OF THE DRAWINGS

Features and advantages of the claimed subject matter will be apparent from the following detailed description of some example embodiments consistent therewith, which description should be considered with reference to the accompanying drawings, wherein:

FIG. 98 generally illustrates a close up region of the implant delivery system of FIG. 9A:

FIGS. 23 and 24 show an assembled and unassembled view of the implant system of FIG. 20, respectively, in accordance with an embodiment of the present disclosure;

FIG. 25 shows a cross-sectional view of another embodiment of the implant system of FIG. 20;

FIGS. 30-32 show various top plan views of an anchor portion that may be utilized in accordance with at least one embodiment of the present disclosure;

DETAILED DESCRIPTION

Figures 1, 2, 3:
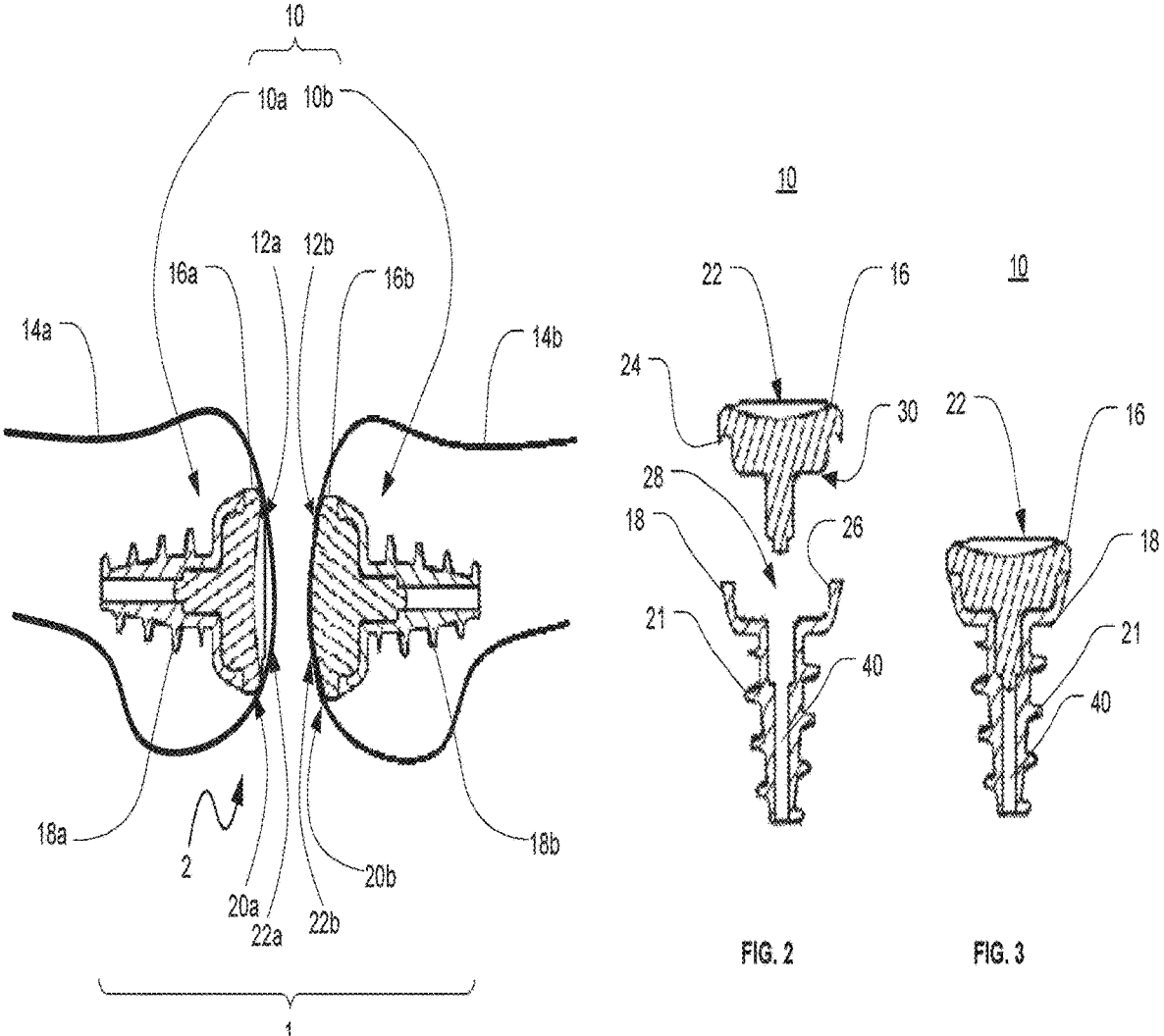
FIG. 1 generally illustrates a total joint replacement system installed in a patient's joint consistent with at least one embodiment of the present disclosure.
FIGS. 2 and 3 generally illustrate one embodiment of an implant system which may be used with the total joint replacement system consistent with at least one embodiment of the present disclosure.

With reference to FIG. 1, one embodiment of total joint replacement system 1 installed in a patient's joint 2 is generally illustrated. The total joint, replacement system 1 may include two or more implant systems 10 (e.g., a first and a second implant system 10a, 10b) installed in the articular surface 12a, 12b of a patient's bone 14a, 14b, respectively. Each one of the implant systems 10 is configured to repair and/or replace the articular surface 12a and/or 12b (referred to as articular surface 12 for simplicity) of a respective one of the patient's bones 14a and/or 14b (referred to as bone 14 for simplicity). The total joint replacement system 1 may be used with implant systems 10 for replacing any articular surface 12 such as, but not limited to, shoulder joints (e.g., but not limited to, the glenohumeral joint), hip joints (e.g., but not limited to, the acetabulofemoral joint), foot and/or hand joints (e.g., but not limited to, metacarpophalangeal joints, metatarsophalangeal joints, and/or interphalangeal joints), knee joints, elbow joints, or the like. One or more of the implant systems 10 may include total joint implants (wherein all or substantially all of the articular surface of at least one bone is replaced with the artificial surface of the implant) and/or partial implants (wherein substantially only the damaged portion(s) of the articular surface 12 of a bone 14 is replaced with the artificial surface of the implant). As explained herein, the implant systems 10a, 10b as illustrated in FIG. 1 are for illustrative purposes only, and the total joint replacement system 1 may be used with any implant system 10 as described herein.

Turning now to FIGS. 2-3, one embodiment of an implant system 10 which may be used with the total joint replacement system 1 consistent with the present disclosure is generally illustrated. For example. FIG. 2 generally illustrates one embodiment of an exploded, unassembled implant system 10, and FIG. 3 generally illustrates an assembled implant system 10. The implant system 10 may generally include an implant (e.g., implant body) 16 configured to be secured to an anchor 18. The anchor 18 is configured to be secured to the bone 14 within an excision site 20 formed beneath the patient's articular surface 12 such that a load bearing surface 22 of the implant 16 is generally flush with the patient's surrounding articular surface 12 as generally illustrated in FIG. 1.

The load bearing surface 22 may have any surface contour depending on the intended application. The load bearing surface 22 may be based on or generally correspond to the original contour of the patient's removed articular surface. For example, the load bearing surface 22 may have a contour substantially corresponding to or based on the contour of an articular surface of a patient being repaired. The contour of the load bearing surface 22 may be based on a plurality of measurements taken at the patient's articular surface (for example, using a measuring and/or mapping tool as generally described in U.S. Pat. Nos. 6,520,964, 6,610,067, 6,679, 917, 7,029,479 and 7,510,558, which are fully incorporated herein by reference) and/or may be based on one or more templates.

The load bearing surface 22 may be based on two or more curvatures, for example, the anterior-posterior curvature and the superior-inferior curvature. One or more of the anterior-posterior and/or superior-inferior curvatures may themselves be based on multiple curves, (for example, as generally described in U.S. patent application Ser. No. 12/027, 121, filed Feb. 6, 2008 and entitled System and Method for Joint Resurface Repair, which is fully incorporated herein by reference).

While the load bearing surface 22 in FIGS. 2 and 3 is illustrated having a generally convex contour, it should be appreciated that the load bearing surface 22 is not limited to this configuration and will depend on the intend application. For example, the load bearing surface 22 may include, but is not limited to, generally concave configurations (e.g., as generally illustrated in FIG. 1) and/or generally hemi-spherical shapes.

The excision site 20 may be formed using any method and system known to those skilled in the an, such as, but not limited to, as the systems and methods as described in U.S. Pat. Nos. 6,520,964, 6,610,067, 6,679,917, 7,678,151, 7,896,883, 8,177,841, and 8,388,624, as well as U.S. Publication No. 2010/0368238, all of which are fully incorporated herein by reference. According to one embodiment, the anchor 18 may be secured to the bone 14, for example, using one or more external threads, ribs, protrusions, bone cement, barbs, grooves or any other structure 21 that enables the anchor 18 to be secured to the bone 14. The use of threads 21 as generally illustrated may advantageously allow the height of the implant 12 to be adjusted by rotating the anchor 18 within the bone 14 such that the implant 16 is flush with the surrounding articular surface 12.

The anchor 18 is configured to engage and/or secure the implant assembly 10 to the patient's bone as described herein. Anchor 18 includes a proximal and a distal end region, and optionally may include a cannulated passageway 40. The cannulated passageway 40 may be configured to be advanced over a guide wire (not shown) extending outwardly from the excision site in the bone as generally described in U.S. Pat. Nos. 6,520,964, 6,610,067, 6,679,917, and 7,678,151, all of which are fully incorporated herein by reference. The use of a cannulated passageway 40 and the guide wire may facilitate alignment of the anchor 30 with respect to the excision site and the surrounding articular surface.

As discussed above, the implant 16 may be secured to the anchor 18 by way of a connection. For example, the implant 16 may include at least one first fixation element 24 configured to engage with at least one second fixation element 26 of the anchor 18 to secure the implant 16 to the anchor 18. According to one embodiment, the first and the second fixation elements 24, 26 may include one or more recesses, groves, slots or the like configured to corresponding to one or more protrusions, ribs, barbs, or the like, for example, in a snap-fit arrangement in which the first and/or second fixation elements resiliently deflect. The first and second fixation elements 24, 26 may be disposed about the entire perimeter/periphery of the implant 16 and anchor 18, and/or about one or more regions of the perimeter/periphery. The first and second fixation elements 24, 26 may prevent the implant 16 from becoming free relative to the anchor 18 (for example, to prevent axial and/or rotational movement of the implant 16 relative to the anchor 18). Optionally, the implant 16 may be at least partially received in an implant cavity 28 formed in the anchor 18 such that a bone facing surface 30 of the implant 16 engages against at least a portion of the implant cavity 28, thereby preventing the implant 16 from moving distally when a force is applied to the load bearing surface 22.

It should be appreciated that while the first and second fixation elements 24, 26 are generally illustrated as a recess and a protrusion, respectively, the implant system 10 consistent with the present disclosure is not limited to this arrangement unless specifically claimed as such. For example, the first and second fixation elements 24, 26 may include a protrusion and a recess, respectively, as well as other embodiments. Additionally, the anchor 18 may optionally include a passageway 40, for example, a longitudinal passageway, configured to be advanced over a guide wire (not shown) as generally described in U.S. Pat. Nos. 6,520, 964, 6,610,067, 6,679,917, 7,678,151, 7,896,883, 8,177,841, and 8,388,624, as well as U.S. Publication No. 2010/ 0368238, all of which are fully incorporated herein by reference. For example, the anchor 18 may be inserted into bone 14 or may be inserted into a shaft drilled in the bone 14 to reduce risks or complications arising from the insertion of the anchor 18. Without limitation, a pilot hole may be formed in the bone 14 for receiving the anchor 18 prior to installing the anchor 18. A diameter of the pilot hole may be smaller than the anchor 18, although example embodiments may vary and are not limited thereto.

Figure 4:
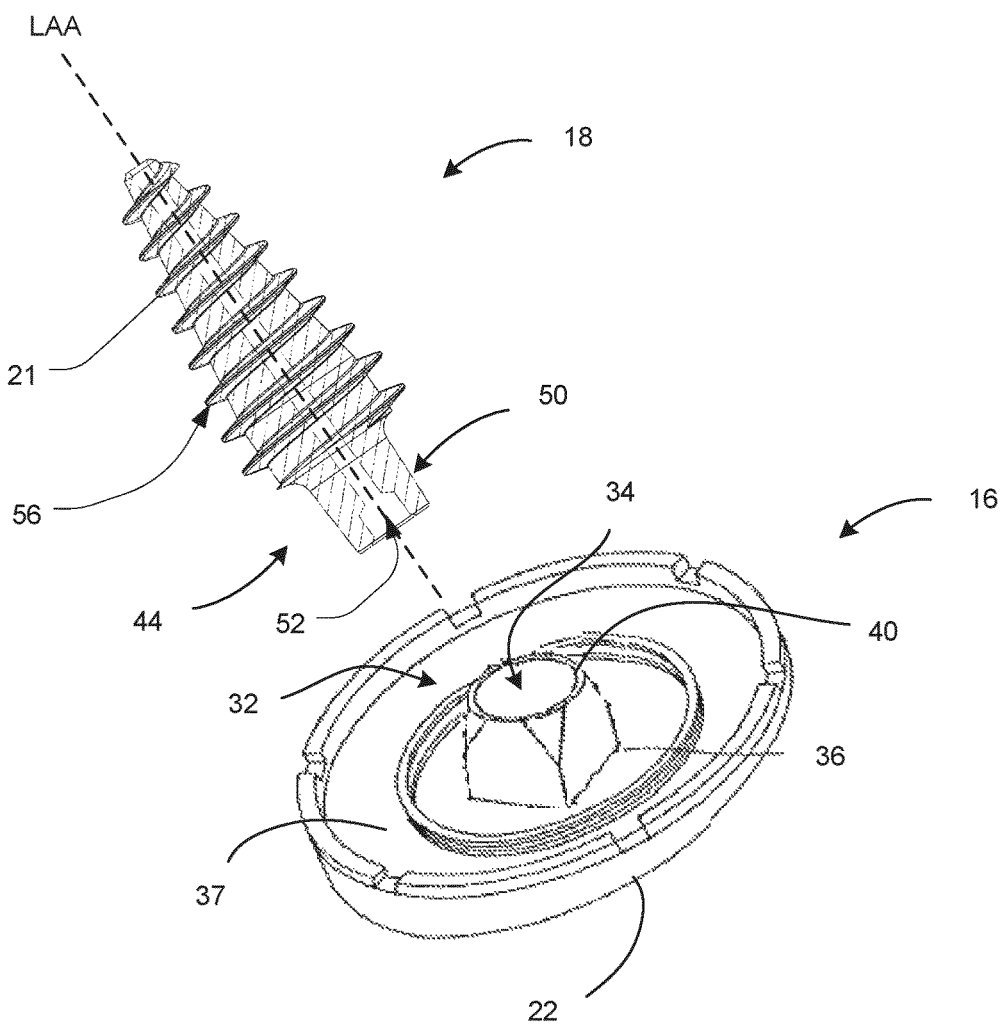
FIG. 4 generally illustrates another embodiment of an implant system which may be used with the total joint replacement system consistent with at least one embodiment of the present disclosure.

Turning now to FIG. 4, another embodiment of an implant system 10 which may be used with the total joint replacement system 1 consistent with the present disclosure is generally illustrated. Implant system 10 includes an implant (e.g., implant body) 16 configured to be secured to an anchor 18. Implant 16 may be formed of a plastic composition and may more particularly comprise, essentially consist of, or consist of a plastic composition. Exemplary plastic compositions may comprise thermoplastic compositions such as polyether ether ketone (PEEK) and polyethylene (PE), including ultrahigh molecular weight polyethylene (UHMWPE) and high density polyethylene (HDPE). In other embodiments, implant 16 may be formed of a metal composition and may more particularly comprise, essentially consist of, or consist of a metal composition, Exemplary metal compositions may comprise stainless steel, titanium, aluminum, chromium cobalt, and/or any alloy thereof.

Implant 16 has a joint facing side including a load bearing (joint articulation) surface 22 having any contour as described herein, and a bone facing surface 37. Bone facing surface 37 may substantially correspond to a contour of an excision site 20 (FIG. 1) formed in an articular surface 12 of a patient. More particularly, a perimeter of the implant 20 may substantially corresponds to a perimeter of an excision site 20 formed in the articular surface 12.

Bone facing surface 37 includes a first fixation element 32. First fixation element 32 comprises a fixation recess 34 formed in a fixation base 36 of implant 16. As shown, fixation recess 34 is substantially cylindrical and may be centered around a longitudinal axis LAA of the anchor 18. More particularly, the sidewall 40 of fixation recess 34 is tapered The anchor 18 is configured to engage and/or secure the implant assembly 10 to the patient's bone as described herein, for example, using threads 21 and/or bone cement. The proximal end region of the anchor 18 includes a second fixation element 44 configured to form a connection with the first fixation element 32. As shown by the figures, anchor 18 may comprise a screw with a fully or partially threaded tapered or non-tapered cylindrical shank which is arranged substantially transverse to the overlying portion of the load bearing surface 22.

As discussed herein, second fixation element 44 is configured to engage with the first fixation element 32 to form a connection therebetween. In the illustrated embodiment, the second fixation element 44 includes a tapered (male) protrusion. The tapered protrusion includes a tapered sidewall 50 configured to contact and abut against at least a portion of a tapered sidewall 40 of the first fixation element 32 to form a frictional connection therebetween. Of course, it should be appreciated that the arrangement of the male and female tapers with respect to the first and second fixation elements 32, 44 may be switched (e.g., the first fixation element 32 may include a male taper and the second fixation element 44 may include a female taper).

The proximal end region of the anchor 30 may also include a driver receptacle 52 arranged to receive a drive member therein, particularly to drive the first anchor 30 into bone. For example, driver receptacle 52 may be arranged to receive a drive member (not shown) to cause one or more anchor elements 56 of the anchor 18 to engage the bone 14. The driver receptacle 52 may allow torque to be transmitted to the anchor 18 to rotate the anchor 18 such that one or more external screw (helical) threads 21 threadably engage and connect with the bone 14.

Elongated anchor 18 may be formed of a plastic composition and may more particularly comprise, essentially consist of, or consist of a plastic composition. Exemplary plastic compositions may comprise thermoplastic compositions such as polyether ether ketone (PEEK) and polyethylene (PE) such as ultrahigh molecular weight polyethylene (UHMWPE) and high density polyethylene (HDPE). In other embodiments, anchor 18 may be formed of a metal composition and may more particularly comprise, essentially consist of, or consist of a metal composition. Exemplary metal compositions may comprise stainless steel, titanium, aluminum, chromium cobalt, and/or any alloy thereof.

Figure 5:
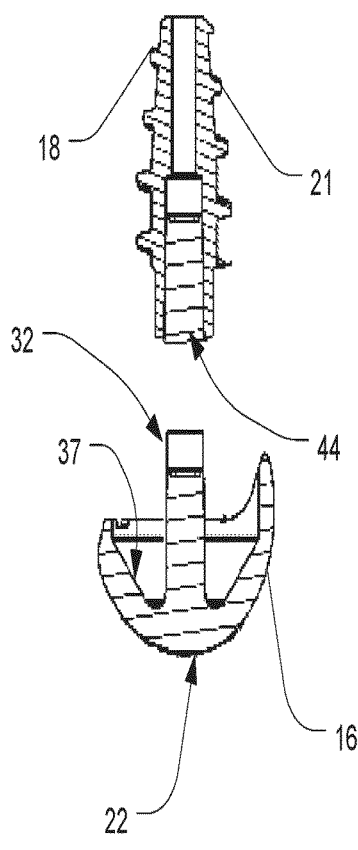
FIGS. 5 and 6 generally illustrate a further embodiment of an implant system which may be used with the total joint replacement system consistent with at least one embodiment of the present disclosure.
Figure 6:
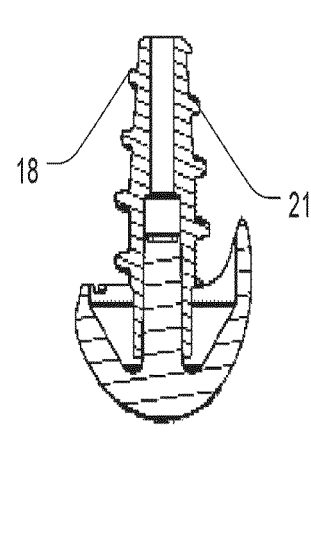
Figures 7A, 7B, 7C, 7D, 7E:
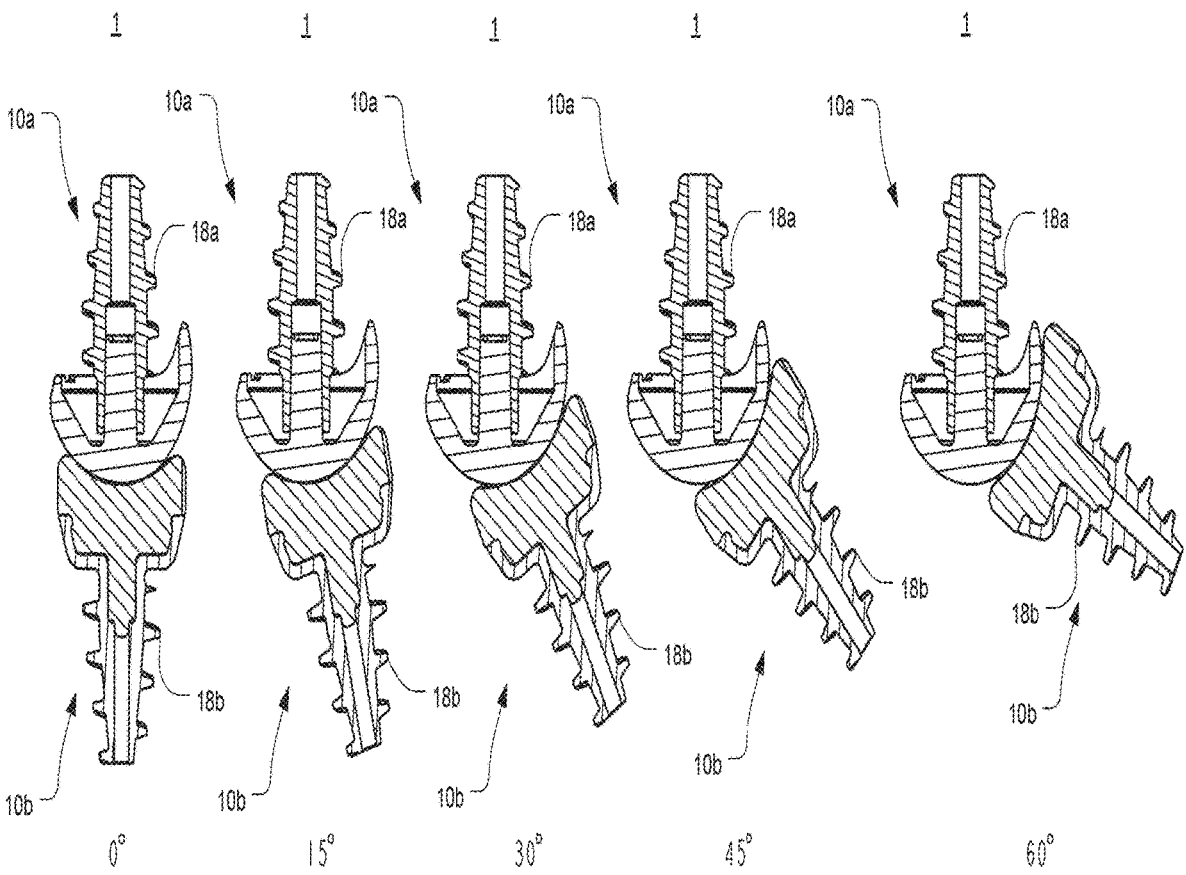
FIGS. 7a-7e generally illustrate cross-sectional views of another embodiment of the total joint replacement system consistent with at least one embodiment of the present disclosure at different angles.

Turning now to FIGS. 5-6, yet another embodiment of an implant system 10 which may be used with the total joint replacement system 1 consistent with the present disclosure is generally illustrated. For example. FIG. 5 generally illustrates one embodiment of an exploded, unassembled implant system 10, and FIG. 6 generally illustrates an assembled implant system 10. Implant 16 has a load bearing surface 22 and a bone facing surface 37. The load bearing surface 22 may have contour as described herein, for example, the original contour of the patient's articular surface generally corresponding to a plurality of overlapping excision sites (e.g., if replacing the dorsal socket or the like). The bone facing surface 37 may also include a first fixation element 32 configured to be secured to a second fixation element 44 of the anchor 18 to form a connection therebetween. In the illustrated embodiment, the first fixation element 32 includes a tapered (male) protrusion and the second fixation element 44 includes a tapered recess. The tapered protrusion includes a tapered sidewall configured to contact and abut against at least a portion of a tapered sidewall of the tapered recess to form a frictional connection therebetween. Of course, it should be appreciated that the arrangement of the male and female tapers with respect to the first and second fixation elements 32, 44 may be switched (e.g., the first fixation element 32 may include a female taper and the second fixation element 44 may include a male taper).

FIGS. 7a-7e generally illustrate cross-sectional views of another embodiment of the total joint replacement system 1 consistent with the present disclosure at different angles, e.g., ranging between 0° and 60°. The total joint replacement system 1 includes a first implant system 10a as generally described herein with respect to FIGS. 5 and 6, and a second implant system 10b as generally described herein with respect to FIGS. 2 and 3. For the sake of clarity, the bones of the joint are not illustrated.

The anchors 18a of the first implant system 10a may be secured to bone as described herein. For example, the height of the anchor 18a may be adjusted by rotating the anchor 18a. Optionally, a trial guide (not shown) may be coupled to the anchor 18a to allow the surgeon to verify that the load bearing surface 22 is substantially flush with the surrounding articular surface (if present) and/or generally corresponds to the location of the original articular surface.

The anchor 18b of the second implant system 10b may also be secured to the bone as described herein. Similarly, the height the anchor 18b may be adjusted by rotating the anchor 18b, and optionally using an implant trial guide (not shown). One advantage of the total joint replacement system 1 is that the height of the anchors 18a, 18b may be infinitely adjusted, and once adjusted to the desired height, the implant 16a, 16b may be secured to the anchors 18a, 18b in the correct orientation. For example, the implant 16a (because it has a non-symmetrical load bearing surface 22) should be aligned in a predetermined orientation with respect to the bone (e.g., the metatarsal bone). Similarly, the implant 16b should be aligned in a predetermined orientation with respect to the phalangeal bone and/or the first implant 16a (e.g., the implant 16b may have a generally convex contour configured to generally align with and slide against the implant 16a as generally illustrated in FIGS. 7a-7e). Thus, the height and/or separation distance between the bones (e.g., metatarsal and phalangeal bones) may be infinitely adjusted without impacting the alignment of the implants 16a, 16b (i.e., the alignment of the implants 16a, 16b may be independent of the position of the anchors 18a, 18b).

Figure 8:
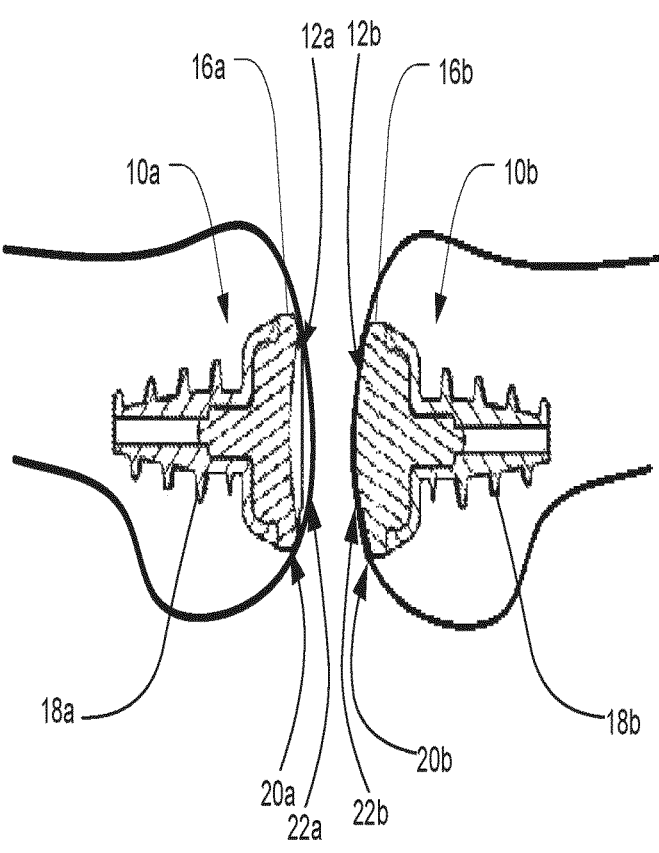
FIG. 8 generally illustrates a further embodiment of an implant system which may be used with the total joint replacement system consistent with at least one embodiment of the present disclosure.

Turning now to FIG. 8, yet another embodiment of the total joint replacement system 1 is generally illustrated. The total joint replacement system 1 includes a first and a second implant system 10a, 10b similar to the implant systems 10 as generally described herein with respect to FIGS. 2 and 3. In particular, the first implant system 10a includes an implant 16a having a generally convex load bearing surface 22a and the second implant system 10b includes an implant 16b having a generally concaved load bearing surface 22b configured to mate with load bearing surface 22a.

Turning now to FIGS. 9-17, systems and methods for securing an anchor 18 into the bone and securing the implant 16 to the anchor 18 using an implant delivery system 100 consistent with the present disclosure are generally illustrated. In a first mode (as generally illustrated in FIGS. 9-13), the implant delivery system 100 may be used to secure the anchor 18 into an excision site formed in the bone. In a second mode (FIGS. 14-17), the delivery system 100 may be used to secure the implant 16 to the anchor 18 to assemble the implant system 10 within the excision site. As may be appreciated, the implant delivery system 100 may be used with any implant system 10 described herein and is not limited to the illustrated implant system 10 unless specifically claimed as such.

Figure 10:
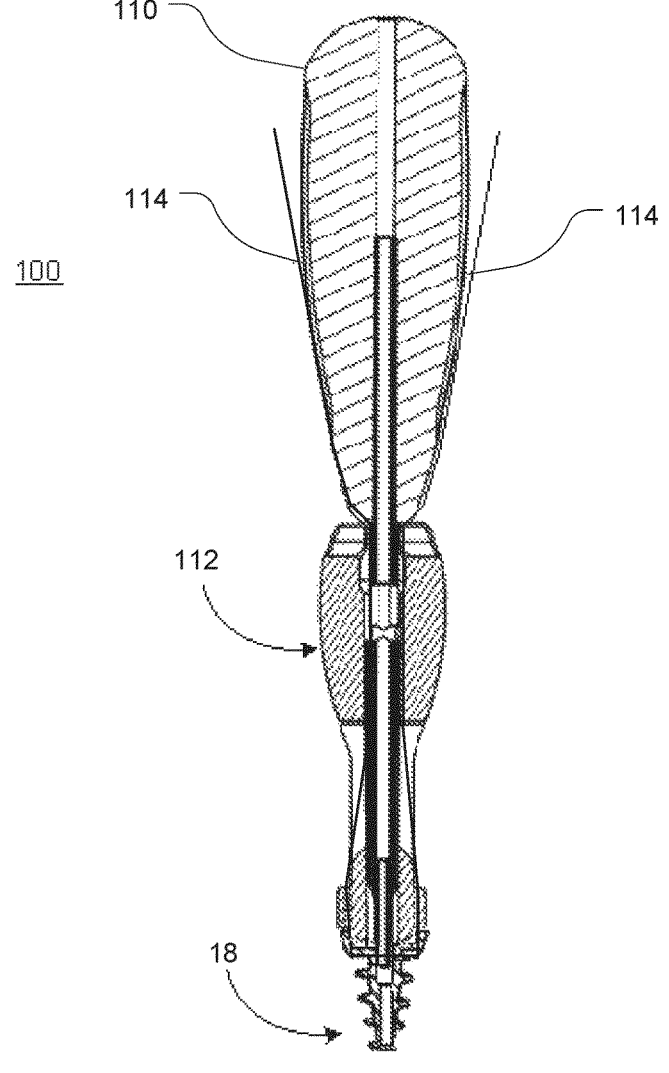
FIGS. 10-12 generally illustrate various steps in the installation of an anchor consistent with at least one embodiment of the present disclosure.
Figure 11:
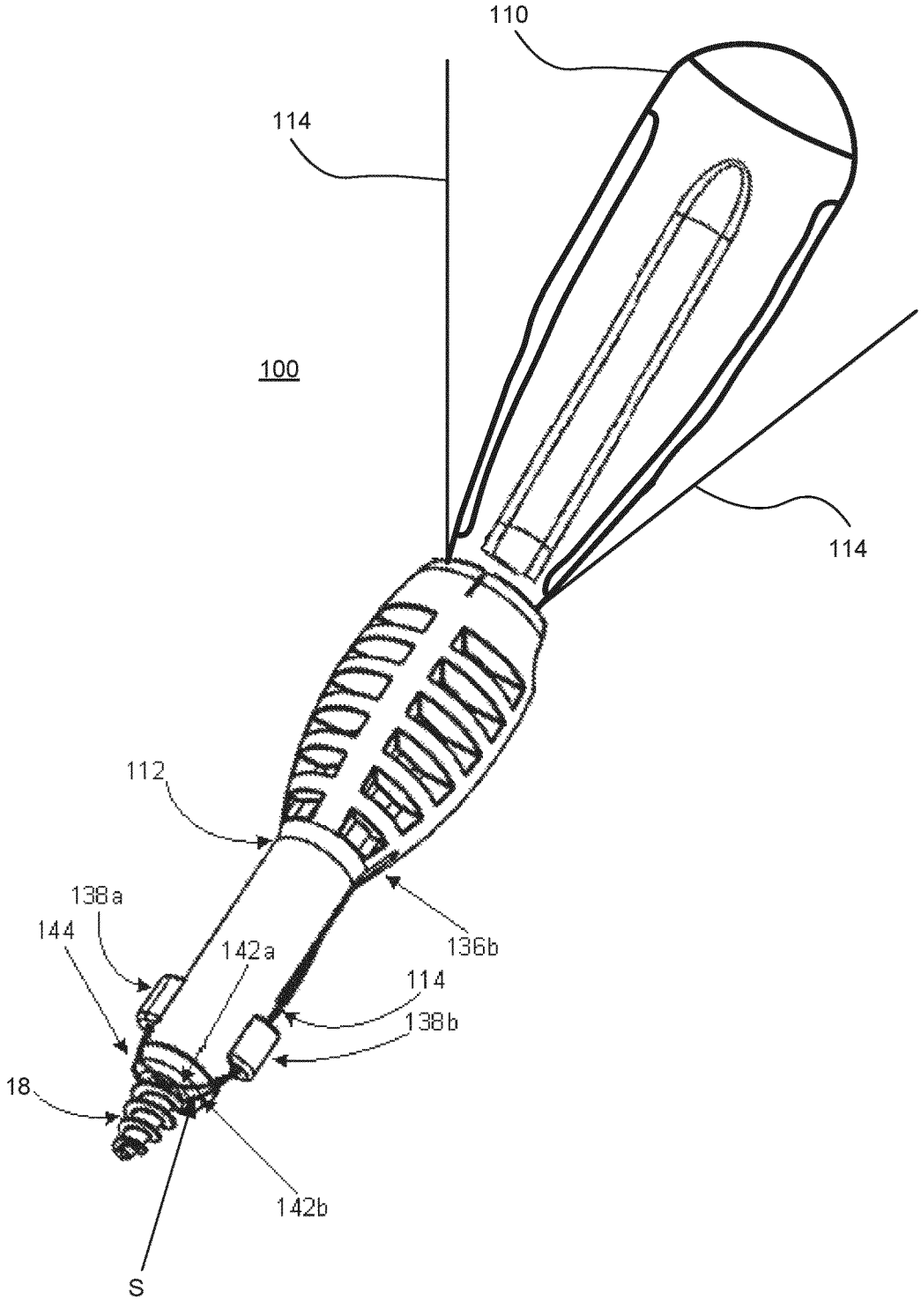
Figure 12:
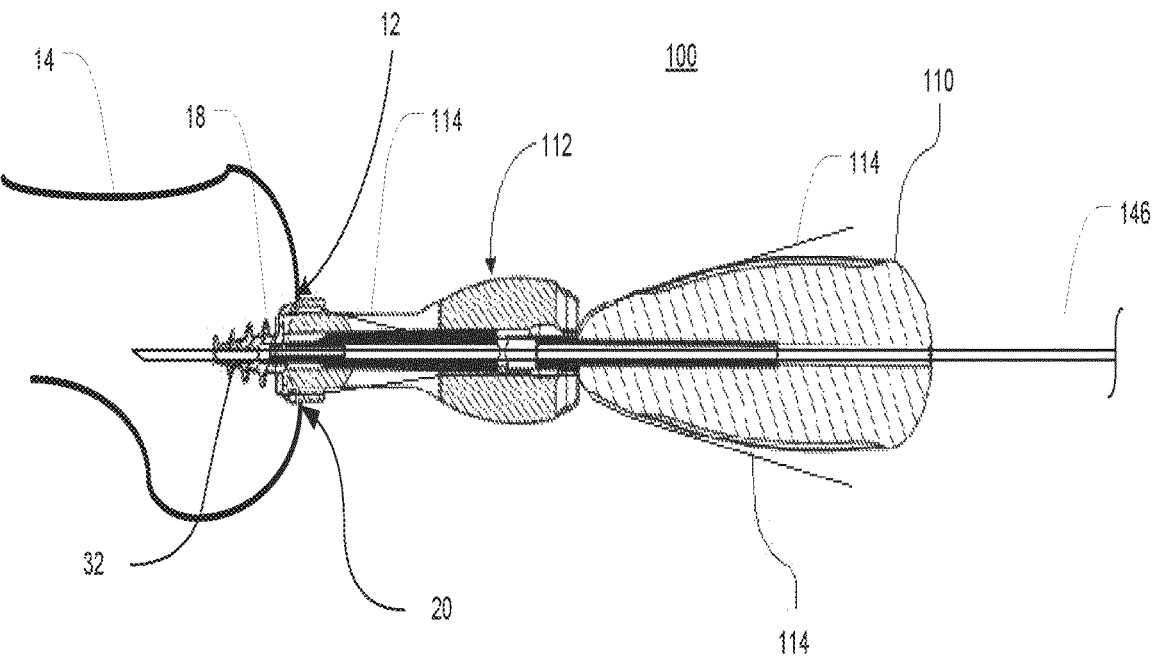
Figure 13:
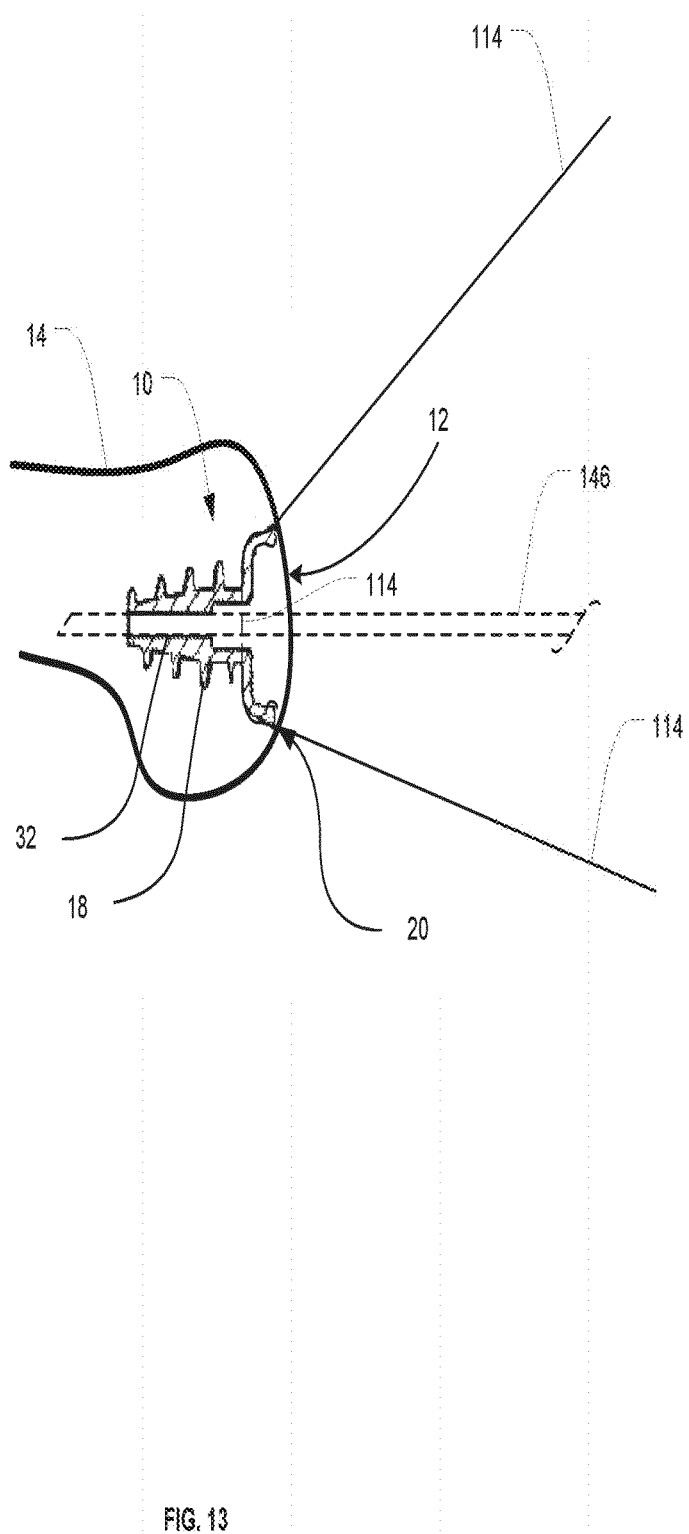
FIG. 13 generally illustrates an anchor secured in the bone consistent with at least one embodiment of the present disclosure.

With reference to FIGS. 9-13, one embodiment of system and method for using the implant delivery system 100 to secure the anchor 18 to bone within an excision site is generally illustrated. The implant delivery system 100 may include a driver 110, a biasing body 112, and at least one suture 114. As explained herein, the implant delivery system 100 may be configured to retain the anchor 18 into engagement with the driver 110 and to secure the anchor 18 to bone 14 within an excision site 20 (as generally illustrated in FIGS. 12 and 13). For example, the driver 110 may be received through the biasing body 112, and the suture 114 may be disposed around a portion of the anchor 18 to provide increased control and/or maintain contact between the driver 110 and the anchor 18 while securing the anchor 18 into the bone 14 within the excision site 20. The excision site 20 may be formed using any method and system known to those skilled in the art.

Figure 9A:
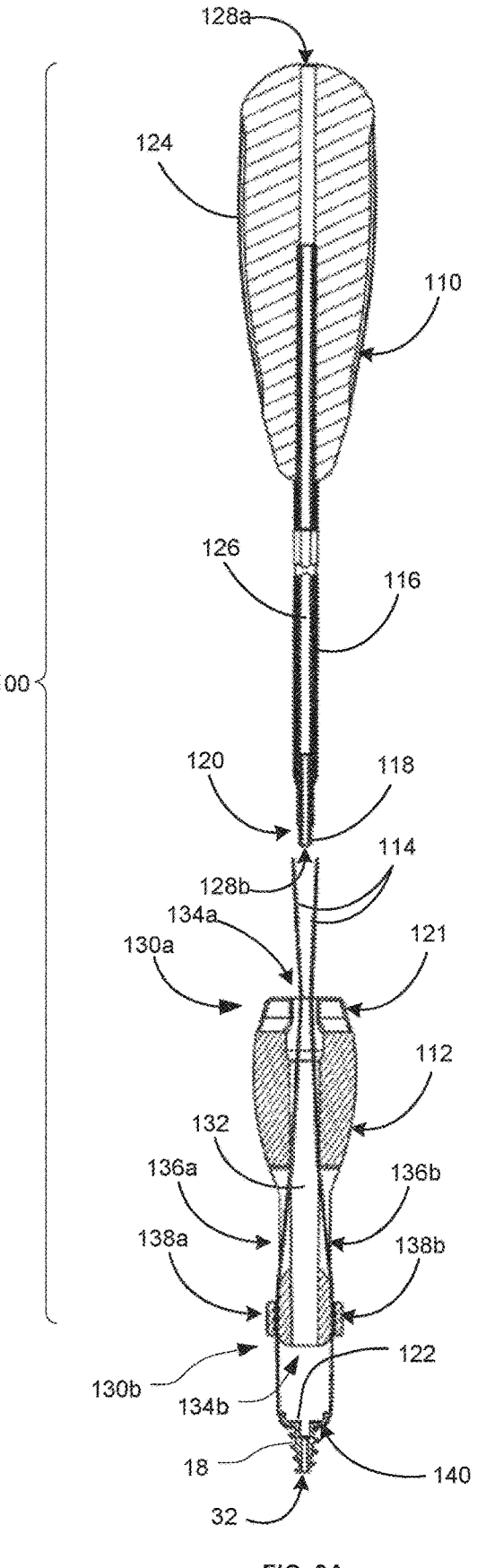
FIG. 9A generally illustrates one embodiment of an implant delivery system which may be used with the total joint replacement system consistent with at least one embodiment of the present disclosure.
Figure 9B:
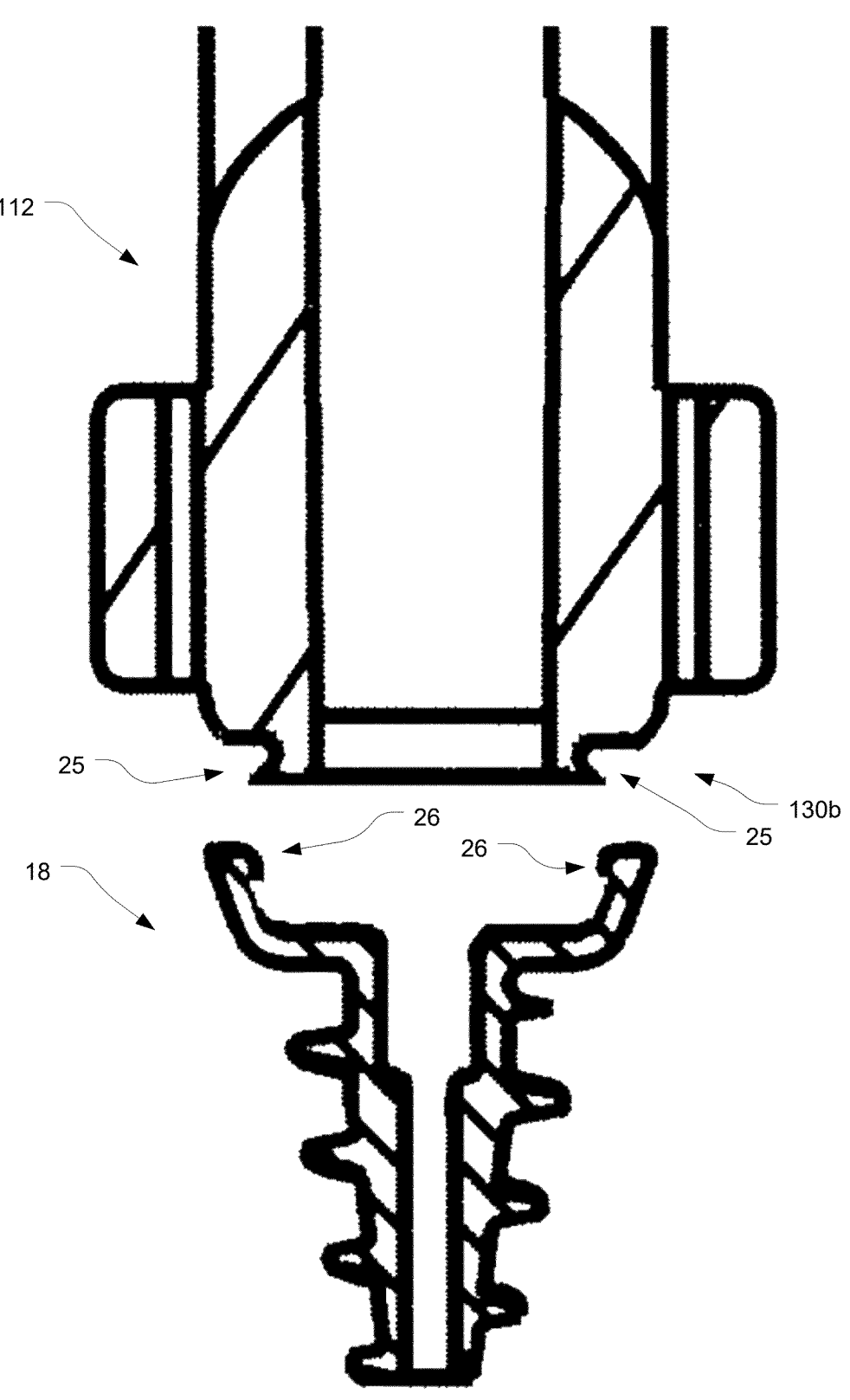

The driver 110, FIG. 9A, includes a longitudinally disposed shaft 116 having an engagement portion 118 disposed about a distal end 120. The engagement portion 118 is configured to be coupled with a corresponding engagement portion 122 of the anchor 18 and to transmit torque as generally illustrated in FIGS. 10-12. For example, the engagement portion 118 may be a male-shaped coupling unit (such as, but not limited to, a splined or hex-shaped driver) configured to couple with a female-shaped coupling unit 122 (such as, but not limited to, a splined or hex-shaped recession formed in the anchor 18) in order to rotate or drive the anchor 18 into the bone. However, the engagement portions 118, 122 may vary and are not limited thereto. For example, the driver 110 may be configured to accept interchangeable bits having a different engagement portion 118 configurations, thereby allowing the engagement portion 118 of the driver 110 to be coupled to the engaging portion 122 of the anchor 18 using several different bits as necessary. Alternatively (or additionally), the engagement portion 118 may have a female-shaped coupling unit and the anchor 18 may have a male-shaped coupling unit. The shape of the engaging portions 118, 122 may be other than splined or hexagonal, and those in the art will recognize that one of any number of shapes or configuration for such components may be employed in a device or method consistent with example embodiments. Optionally, the engagement portion 118 may be magnetized or otherwise configured to maintain contact or control over the anchor 18.

While the engaging portion 122 of the anchor 18 is shown located on an inner wall of the narrow portion of the anchor 18, example embodiments may vary and are not limited thereto. For example, the engaging portion 122 of the anchor 18 may be located on an inner wall of the wide portion of the anchor 18 and/or on an outer wall of either the narrow portion or the wide portion of the anchor 18. Optionally, an intermediate or adapting portion (not shown) may be used to connect the driver 110 to the anchor 18.

The driver 110 may optionally include a handle 124. The handle 124 may facilitate grasping of the driver 110 and may be configured to cause a rotational force or a torque on the shaft 116, which may ultimately impart a rotational force or torque on the anchor 18 to secure the anchor 18 into the bone. The handle 124 may be separate from the shaft 116 (either permanently or removably coupled thereto), or may be a unitary, single piece with the shaft 116. While the handle 124 is illustrated as having a larger width than the shaft 116, example embodiments may vary and are not limited thereto. For example, the handle 124 may include a lever arm or may be configured to couple to a lever arm that is used to create the rotational force or torque.

The handle 124 and/or the shaft 116 may be cannulated to define a longitudinal passageway 126. The longitudinal passageway 126 may include proximal and distal openings 128a, 128b configured to be advanced over a guide wire (not shown for clarity), for example, when securing the anchor 18 into the bone within the excision site.

The biasing body 112 defines a shaft passageway 132 extending between a first and a second end region 130a, 130b having a first and second opening 134a, 134b. The shaft passageway 132 is configured to receive at least a portion of the shaft 116 of the driver 110, for example, as generally illustrated in FIGS. 10 and 11. The shaft 116 and the shaft passageway 132 may be configured such that the distal end 120 of the shaft 116 extends beyond the second end 134b of the shaft passageway 132 to allow the engagement portion 118 of the driver 110 to engage the corresponding engagement portion 122 of the anchor 18, for example, as generally illustrated in FIGS. 10 and 11. Optionally, the biasing body 112 may include a driver cradle 121, discussed in greater detail herein, which may be used to secure the implant. 16 (not shown) with the anchor 18.

Additionally, the second end region 130*b* may include a fixation element 25 (FIG. 9B) which substantially corresponds to the first fixation element 24 of the implant 16. In this manner, the fixation element 25 of the second end region 130*b* of the biasing body 112 may be coupled to the second fixation element 26 of the anchor 18 to generally secure the anchor 18 to the biasing body 112. The connection between the biasing body 112 and the anchor 18 may facilitate placement of the anchor 18 within the excision site by creating a generally secure connection therebetween. It may be appreciated, however, that the connection between the fixation element 25 of the second end region 130*b* and the second fixation element 26 of the anchor 18 does not need to be as strong as the connection between the first and second fixation elements 24, 26 since it is only generally intended to help advance the anchor 18 to and align the anchor 18 within the excision site.

Alternatively (or in addition to), the biasing body 112. FIG. 9A, may be configured to receive a suture 114 disposed around (e.g., wrap around) a portion of the anchor 18. Tension may be applied to the suture 114 to generally urge the anchor 18 into contact with the driver 110 and/or the biasing body 112 to provide more control over and/or maintain contact between the driver 110 and the anchor 18. The suture 114 may be configured to extend through and/or around the biasing body 112 in any manner known to those skilled in the art. For example, the suture 114 may extend through the first opening 134*a* of the shaft passageway 132 of the biasing body 112, out through one or more suture apertures/openings/passageways 136*a*, 136*b*, through one or more suture alignment guides 138*a*, 138*b* and around a contact portion 140 of the anchor 18. The suture passageways 136*a*, 136*b* may allow the suture 114 to pass from the exterior of the biasing body 112 to the interior of the shaft passageway 132. While the suture passageways 136*a*, 136*b* are illustrated in the middle of the biasing body 112, example embodiments may vary and are not limited thereto. It should also be appreciated that the suture 114 does not have to pass through the shaft passageway 132, and instead the biasing body 112 may include one or more separate passageways (not shown) for the suture 114.

The suture alignment guides 138*a*, 138*b* are configured to retain the suture 114 about the distal end of the biasing body 112. According to one embodiment, the suture 114 may include a first and a second portion 142*a*, 142*b* (best seen in FIG. 11) which form a basket, cradle, or frame 144 extending about the contact portion of the anchor 18. The first and second portions 142*a*, 142*b* may be formed from two or more pieces of suture, or may be formed from a single piece of suture. The suture alignment guides 138*a*, 138*b* may be configured to prevent the first and second portions 142*a*, 142*b* of the cradle 144 from slipping off the anchor 18 by restricting the separation angle S of the first and second portions 142*a*, 142*b* of the cradle 144.

While the suture alignment guides 138*a*, 138*b* are shown at the distal end of the biasing body 112 nearest the anchor 18, example embodiments may vary and are not limited thereto. For example, the suture alignment guides 138*a*, 138*b* may be located anywhere along the biasing body 112 provided the suture alignment guides 138*a*, 138*b* may prevent the suture 114 from slipping off the anchor 18. Additionally, while the suture alignment guides 138*a*, 138*b* are shown as an exterior protrusion of the biasing body 112 with holes to allow the suture 114 to pass through, example embodiments may vary and are not limited thereto. For example, the suture alignment guides 138*a*, 138*b* may be flush with the biasing body 112 or may protrude in an arc shape, with a gap between one edge of the suture alignment guides 138*a*, 138*b* and the biasing body 112 to allow the suture 114 to enter. It may also be appreciated that the length of the suture alignment guides 138*a*, 138*b* may vary and the suture alignment guides 138*a*, 138*b* may be integrated into the suture passageways 136*a*, 136*b*.

While the contact portion 140 of the anchor 18 is shown on the bottom edge of the anchor 18, example embodiments may vary and the contact portion 140 may be situated anywhere along the anchor 18. For example, the contact portion 140 may also be disposed about the top portion of anchor 18. The contact portion 140 of the anchor 18 may include a flat edge or may include guides, grooves, slots, or channels configured to receive the suture 114. For example, the suture 114 may extend through a passageway formed in the anchor 18 such that a portion of the anchor 18 generally surrounds the suture 114, and the cradle 144 may be eliminated.

To secure the anchor 18 to the bone 14 within the excision site 20, the suture 114 may be received through the biasing body 112 (e.g., through the first opening 134*a* of the shaft passageway 132, out through the suture passageways 136*a*, 136*b*, and through the suture alignment guides 138*a*, 138*b*) such that the cradle 144 is disposed about the contact portion 140 of the anchor 18 as generally illustrated in FIG. 9A. The driver 110 may be advanced through shaft passageway 132 until the engagement portion 118 contacts the corresponding engagement portion 122 of the anchor 18. The suture 114 may then be tensioned to retain the engagement between the driver 110 and the anchor 18, for example, by applying a force against the suture 114 in a direction generally away from the anchor 18 as generally illustrated in FIGS. 10 and 11. Alternatively (or in addition), the fixation element 25 (FIG. 9B) of the biasing body 112 may be secured to the fixation element 26 of the anchor 18, and the driver 110 may engage the anchor 18 as described herein.

With the anchor 18 securely engaged with the driver 110, the anchor 18 may be advanced to and aligned with the excision site 20 (as generally illustrated in FIG. 12) formed in the patient's articular surface 12 and bone 14. Optionally, the anchor 18 may be aligned with the excision site 20 using a guide wire 146 extending outwardly from the bone 14 within the excision site 20. Because the anchor 18 is retained against the driver 110, it is easier for the surgeon to align the anchor 18 relative to the excision site 20. As discussed herein, the anchor 18 may optionally include a cannulated passageway 32 (best seen in FIG. 9A) that is generally aligned with (e.g., generally co-axial) the longitudinal passageway 126 of the driver 110 (as best illustrated in FIG. 12) such that the anchor 18 and the driver 110 (and optionally the biasing device 112) may be advanced over the guide wire 146. The optionally use of the cannulated passageway 32 and the guide wire 146 may further aid in aligning the anchor 18 at the desired angle with respect to the excision site 20 and the surrounding articular surface 12.

Once the anchor 18 is aligned with respect to the excision site 20, the driver 110 may then be used to secure the anchor 18 into the bone 14, for example, by rotating the driver 110, thereby causing the anchor 18 to rotate. The height of the anchor 18 may be verified using a trial gauge (not shown) which may be easily inserted/placed into the anchor 18 to ensure that the implant 16 (e.g., FIG. 1) is substantially flush with the surrounding articular surface 21. Once the height of the anchor 18 is verified, the driver 110 (and optionally the biasing device 112 and/or the guide wire 146) may be removed, leaving the anchor 18 (and optionally the suture 114) remaining in the bone 14, as generally illustrated in FIG. 13. While the anchor 18 is illustrated having threads 21, it may be appreciated that the anchor 18 may be secured to the bone 14 using any device(s) known to those skill in the art including, but not limited to, ribs, barbs, bone cement, porous structures, and the like.

It should also be appreciated that the biasing device 112 does not have to be used when advancing and/or aligning the anchor 18 with respect the excision site 20. For example, the biasing device 112 may be eliminated and tension may be applied to the suture 114 to keep the anchor 18 engaged with the driver 110. Alternatively, the anchor 18 may be advanced to and aligned with the excision site 20 without using the driver 110. For example, the suture 114 may be secured about a portion of the anchor 18, and once the anchor 18 is aligned within the excision site 20, the driver 110 may engage the anchor 18 and used to secure the anchor 18 within the excision site 20 in the bone 14, 21.

Turning now to FIGS. 14-17, systems and methods for securing an implant 16 to the anchor 18 using an implant delivery system 100 consistent with the present disclosure are generally illustrated. As discussed herein, the implant delivery system 100 may be configured to generate a biasing force to secure the implant 16 to the anchor 18 wherein the biasing force is only applied against the implant 16 and the anchor 18, and not the surrounding bone or tissue 14.

Figure 14:
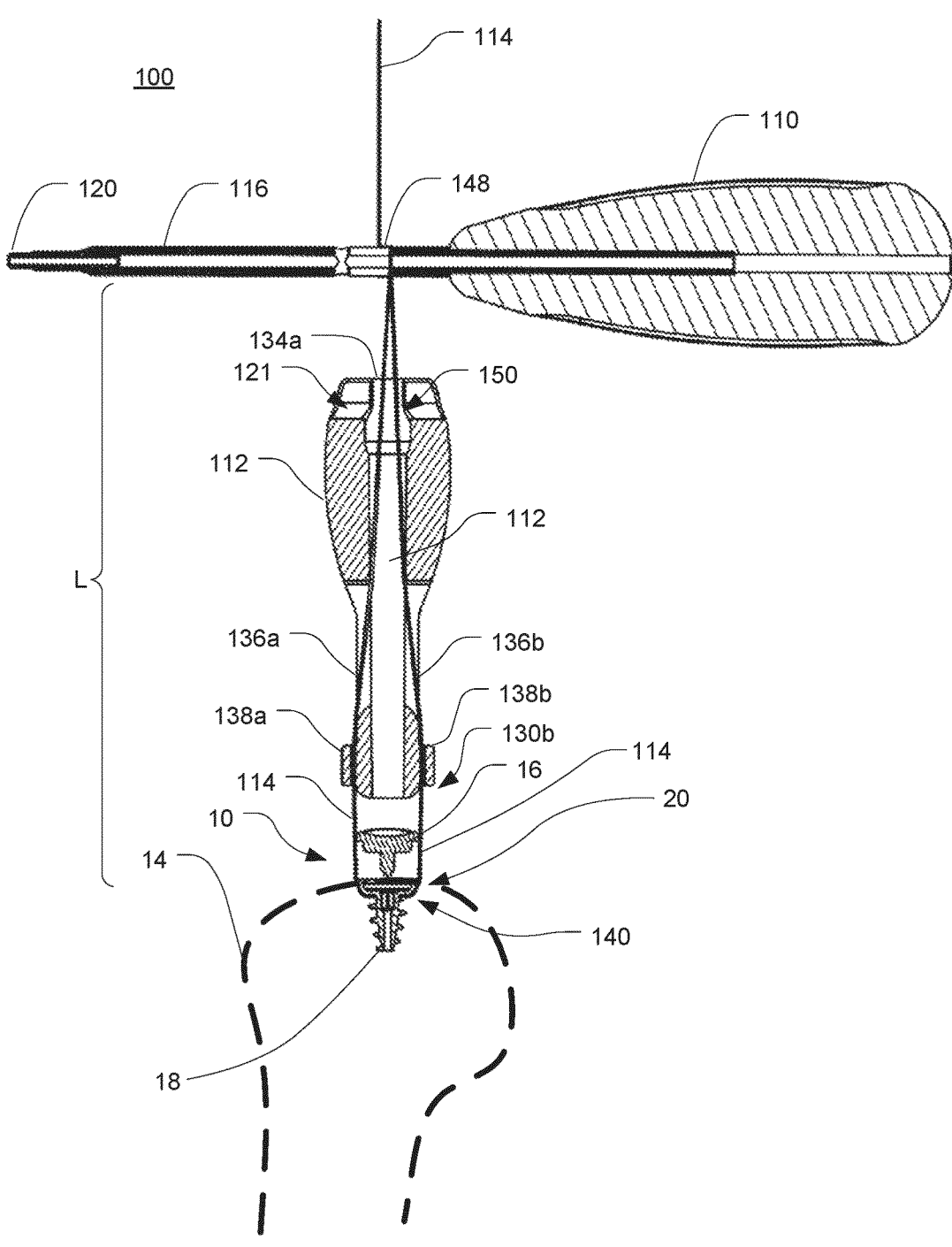
FIGS. 14-17 generally illustrate various steps in the installation/coupling of the implant with an anchor consistent with at least one embodiment of the present disclosure.
Figure 15:
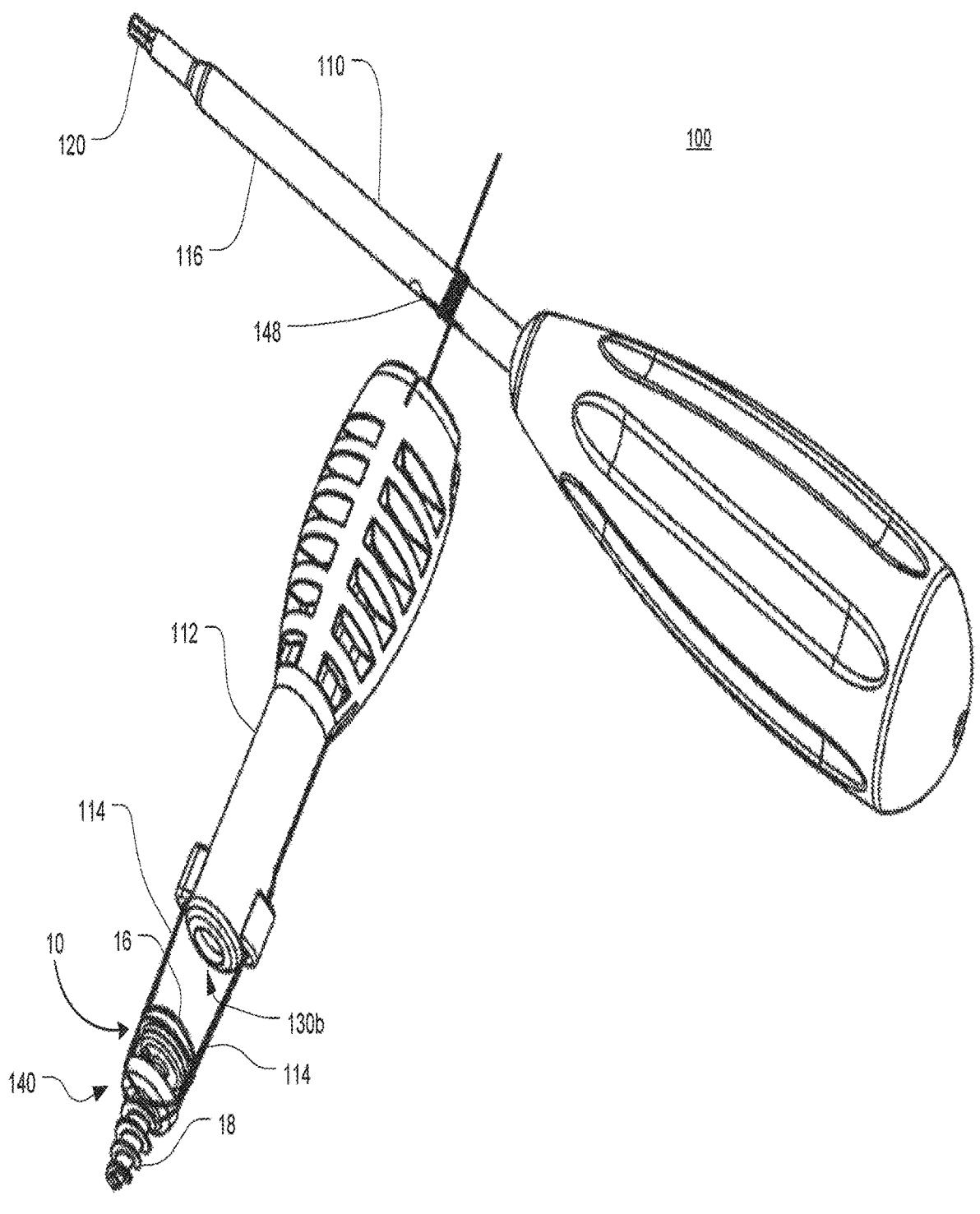

With the anchor 18 secured to the bone 14 and the suture 114 disposed about the contact portion 140 of the anchor 18 as described herein, the implant 16 may be arranged (i.e., placed) between the anchor 18 and the second end region 130*b* of the biasing device 112 as generally illustrated in FIGS. 14 and 15. The suture 114 may extend around the contact portion 140 of the anchor 18, through suture alignment guides 138*a*, 138*b* and suture passageways 136*a*, 136*b*, and exit through the first opening 134*a* of the shaft passageway 132 of the biasing body 112. The suture 114 may also be generally coupled or secured to a portion of the driver 110, for example, a portion of the shaft 116. For example, the driver 110 may include a suture engagement 148 configured to allow the suture 114 to be generally fixed or retained by the driver 110.

According to one embodiment, the suture engagement 148 may include a hole or aperture through the shaft 116. At least a portion of the suture 114 may pass through the hole 148, and the suture 114 may be secured within the suture engagement 148 as the driver 110 is rotated to reduce the length L of the suture 114 between the driver 110 and the anchor 18 as explained herein. It should be appreciated that the suture engagement 148 may include any device for generally securing the suture 114 to the driver 110. For example, the suture engagement 148 may include an external protrusion, a groove, non-cylindrical region, and/or a slot configured to secure the suture 114. Alternatively, the suture 114 may be wrapped around the shaft 116, and the tension generated by the rotation of the driver 110 may secure the suture 114 thereto. The length of the biasing body 112 may be selected to allow the surgeon sufficient room to rotate the driver 110, and therefore may depend on the intended application.

With the suture 114 generally secured to the driver 110, the driver 110 may be rotated about its longitudinal axis A as it is received within the driver cradle 121. The driver cradle 121 may be configured to receive the driver 110 (e.g., the shaft 116) and generally retain the shaft 116 as the shaft

116 is rotated relative to the biasing body 112. For example, the driver cradle 121 may include one or ore recesses, grooves, or lips formed in the first end region 134*a* of the biasing body 112. The driver cradle 121 may also include one or more holes or passageways formed through the biasing body 112 configured to receive and generally retain the shaft 116.

Optionally, the driver cradle 121 may include an enlarged opening 150 (best seen in FIG. 9). As the driver 110 is rotated, the suture 114 begins to wrap around the shaft 116, thereby increasing the diameter of the shaft 116. The enlarged opening 150 provides a void space that the suture 114 can pass through as the driver 110 is rotated and the suture 114 builds up around the shaft 116. As a result, the suture 114 may generally avoid contact with the driver cradle 121, and the torque necessary to rotate the driver 110 may be reduced.

Figure 16:
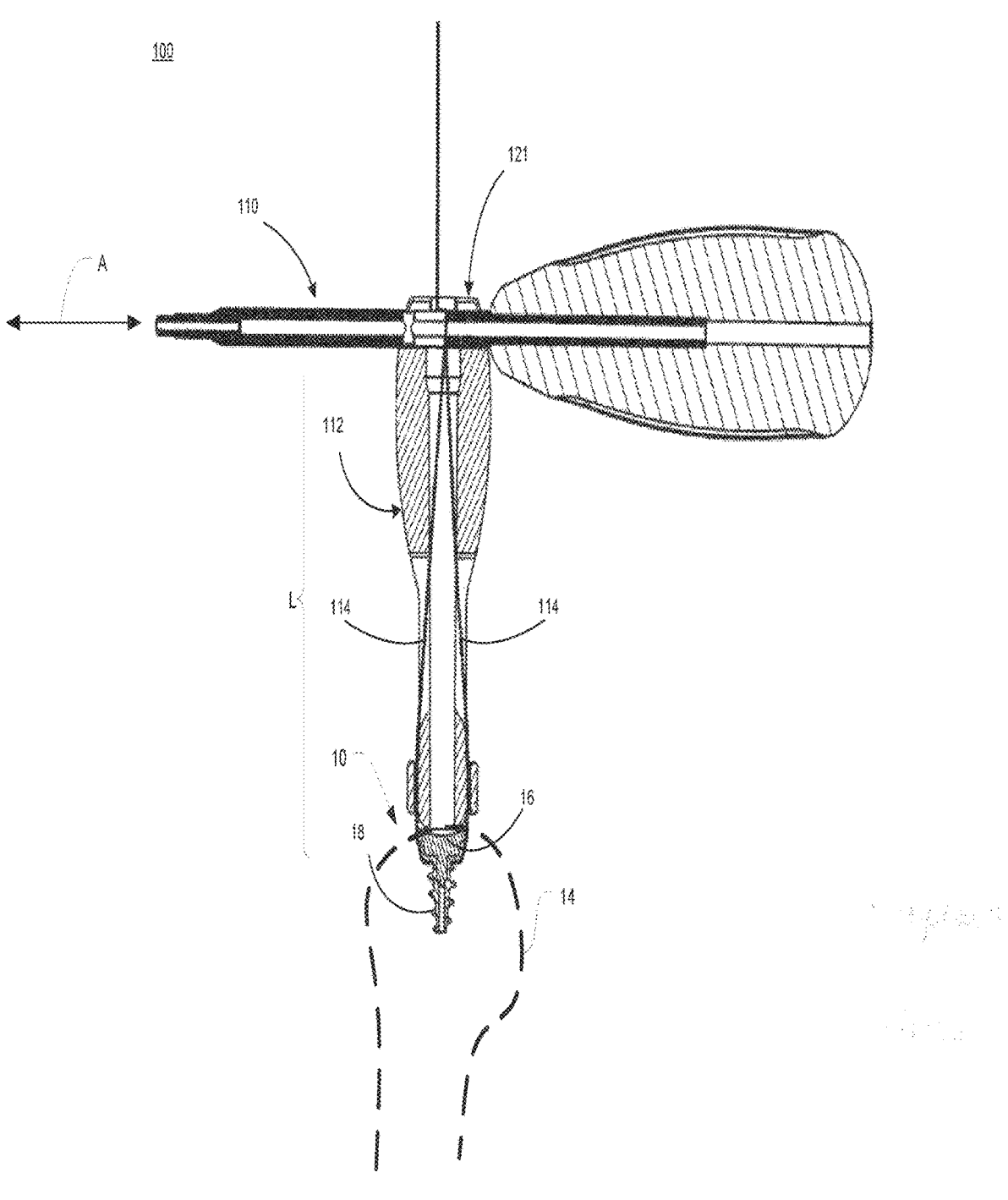
Figure 17:
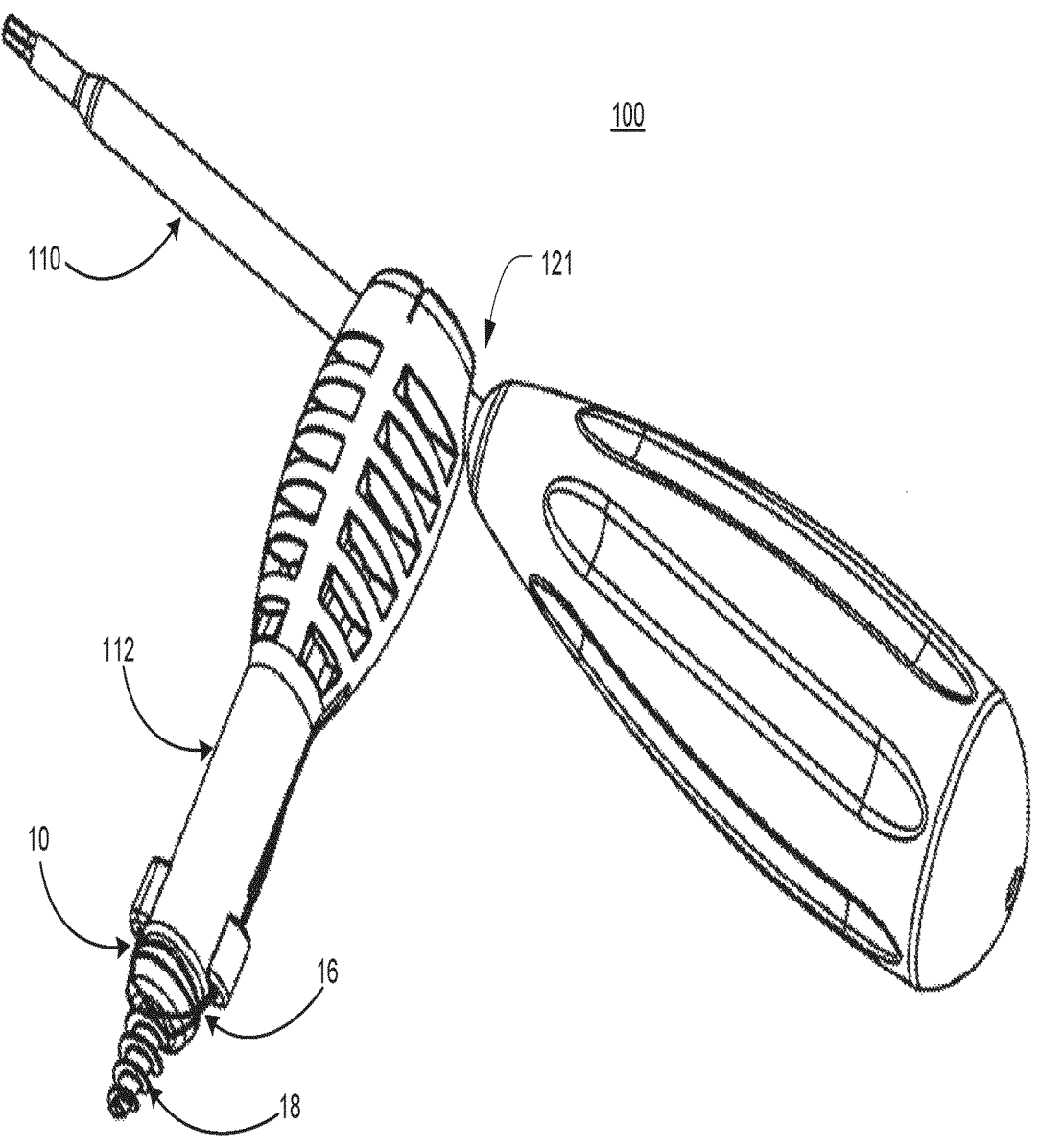

Turning now to FIGS. 16 and 17, with the implant 16 disposed between the anchor 18 and the second end region 132*b* of the biasing body 112, and the driver 110 (along with the suture 114 generally secured thereto) disposed within the driver cradle 121, the surgeon may rotate the driver 110 about longitudinal axis A to reduce the length L of the suture 114 extending between the driver 110 and the contact portion 120 of the anchor 118. The reduction in the length L of the suture 114 generates a biasing force which urges the implant 16 into engagement with the anchor 18. As may be appreciated, the implant delivery system 10) generates a biasing force which is applied against the implant 16 and anchor 18 through the suture 114 only (i.e., substantially no force is applied to the surrounding bone 14 or tissue).

More specifically, because the suture 114 supports the anchor 18, rotation of the driver 110 about longitudinal axis A increases the tension on the suture 114 (and therefore the biasing force between the implant 16 and the anchor 18) in an opposite direction of the downward force being placed upon the implant 16 by the biasing body 112. Continued rotation of the driver 110 increases the biasing force between the implant 16 and the anchor 18 and, once the biasing force exceeds the required threshold to install the implant 16, the implant 16 may be successfully installed (e.g., secured) in the anchor 18. Thus, as a result of the suture 114 applying a relatively equal and opposite force to the anchor 18 and the biasing device 110 (and therefore the implant 16), the underlying bone 14 and other structures are not affected, preventing or reducing potential injury from securing the implant 16 into the anchor 18. The implant delivery system 100 therefore avoids and/or reduces any impact to the bone 14 (e.g., eliminates blunt force due to a hammer/mallet or the like), and therefore avoids and/or reduces damage to the bone 16.

Because the biasing force is not transmitted/applied into the surrounding bone 14 or tissue, the implant delivery system 100 may be used with small bones (such as, but not limited to, phalange bones and/or metatarsal bones in the foot and/or hands. Additionally, because the implant delivery system 100 is capable of generating high biasing forces without transmitting/applying the biasing force to the surrounding bone 14 or tissue, the connection between the implant body 16 and the anchor 18 (e.g., first and second fixation elements 24, 26 as discussed herein) may be stronger and more robust, thereby increasing the life expectancy of the implant system 10. Moreover, the implant delivery system 10) may deliver the biasing force uniformly to the implant 16 and be self-leveling or self-aligning, thereby reducing and/or eliminating the difficulties associated with aligning the implant 16 with respect to the anchor 18.

Once the implant 16 is secured to the anchor 18, the suture 114 may be removed from the implant system 10. For example, one or more portions of the suture 114 may be cut and the resulting pieces may be removed (e.g., pulled out) from the excision site 20. Alternatively, a first end of the suture 114 may be released and the suture 114 may be pulled through the biasing body 120 by a second end of the suture 114, resulting in the first end traveling through the shaft passageway 132c, through one of the suture passageways 136a, 136b, out one of the alignment guides 138a, 138b, around the anchor 18 and through the second of the alignment guides 138a, 138b and suture passageways 136a, 136b, and the shaft passageway 132. However, example embodiments may vary and are not limited thereto.

If the suture 114 is cut prior to removal, example embodiments may vary and may include the suture 114 having various shapes or loops. For example, the suture 114 may form a basket, or loop to wrap around the anchor 18. This shape may help support the anchor 18 and may increase control over the anchor 18 prior to the suture 114 being wrapped around the driver 110. In this configuration, the loop may extend so that the loop can be severed after installation of the implant system 10.

It may be appreciated that the strength or ruggedness of the snap-fit connection between the implant 16 and the anchor 18 may depend on the selected materials (e.g., the rigidity) and size/dimensions. In general, more rigid (i.e., less deformable) materials and/or larger sizes/dimensions will result in a stronger, more robust connection between the implant 16 and the anchor 18. While a stronger and more robust connection between the implant 16 and the anchor 18 is generally desirable, the resulting force necessary to make the snap-fit connection increases.

Traditionally, the force necessary to secure the implant 16 to the anchor 18 has been generated using a blunt force, e.g., a hammer/mallet or the like. More specifically, with the anchor 18 secured in the bone 14, the surgeon attempts to align the implant 16 relative to the anchor 18 and impacts the implant 16 with the hammer/mallet to force the implant 16 into engagement with the anchor 18. As may be appreciated, however, a substantial amount of force is also applied to the surrounding bone 14, and if the force applied to the bone 14 is too great, the bone 14 may be damaged. Consequently, the strength of the connection between the implant 16 and the anchor 18 may be limited in many applications (e.g., but not limited to, small bones in the hand and foot as well as implant system 10 installed proximate to the perimeter of a bone) by the strength of the surrounding bone 14. Additionally, it may be very difficult for the surgeon to properly align the implant 16 with respect to the anchor 18.

As discussed herein, the implant delivery system consistent with one embodiment of the present disclosure solves this problem by generating a biasing force to secure the implant 16 to the anchor 18 wherein the biasing force is only applied against the implant 16 and the anchor 18. The biasing force generated by the implant delivery system may therefore be applied only to the implant system 10, and not the surrounding bone or tissue 14. An implant delivery system consistent with the present disclosure may also be used to facilitate securing the anchor 18 into the bone 14.

It should be appreciated that the implant system 10 illustrated with respect to FIGS. 9-17 is provided for illustrative purposes, and that the implant delivery system may be used with any multi-piece implant having an anchor that is coupled (either directly or indirectly) to an implant/ implant body. For example, the implant delivery system may be used with implant systems for replacing any articular surface such as, but not limited to, shoulder joints (e.g., but not limited to, the glenohumeral joint), hip joint (e.g., but not limited to, the acetabulofemoral joint), foot and/or hand joints (e.g., but not limited to, metacarpophalangeal joints, metatarsophalangeal joints, and/or interphalangeal joints), or the like. The implant systems may include total joint implants (wherein all or substantially all of the articular surface of at least one bone is replaced with the artificial surface of the implant) and/or partial implants (wherein substantially only the damaged portion(s) of the articular surface of a bone is replaced with the artificial surface of the implant). The implant delivery system may also be used to secure together a multi-piece pin or rod in a bone to facilitate healing of a fracture or broken bone.

Figure 18:
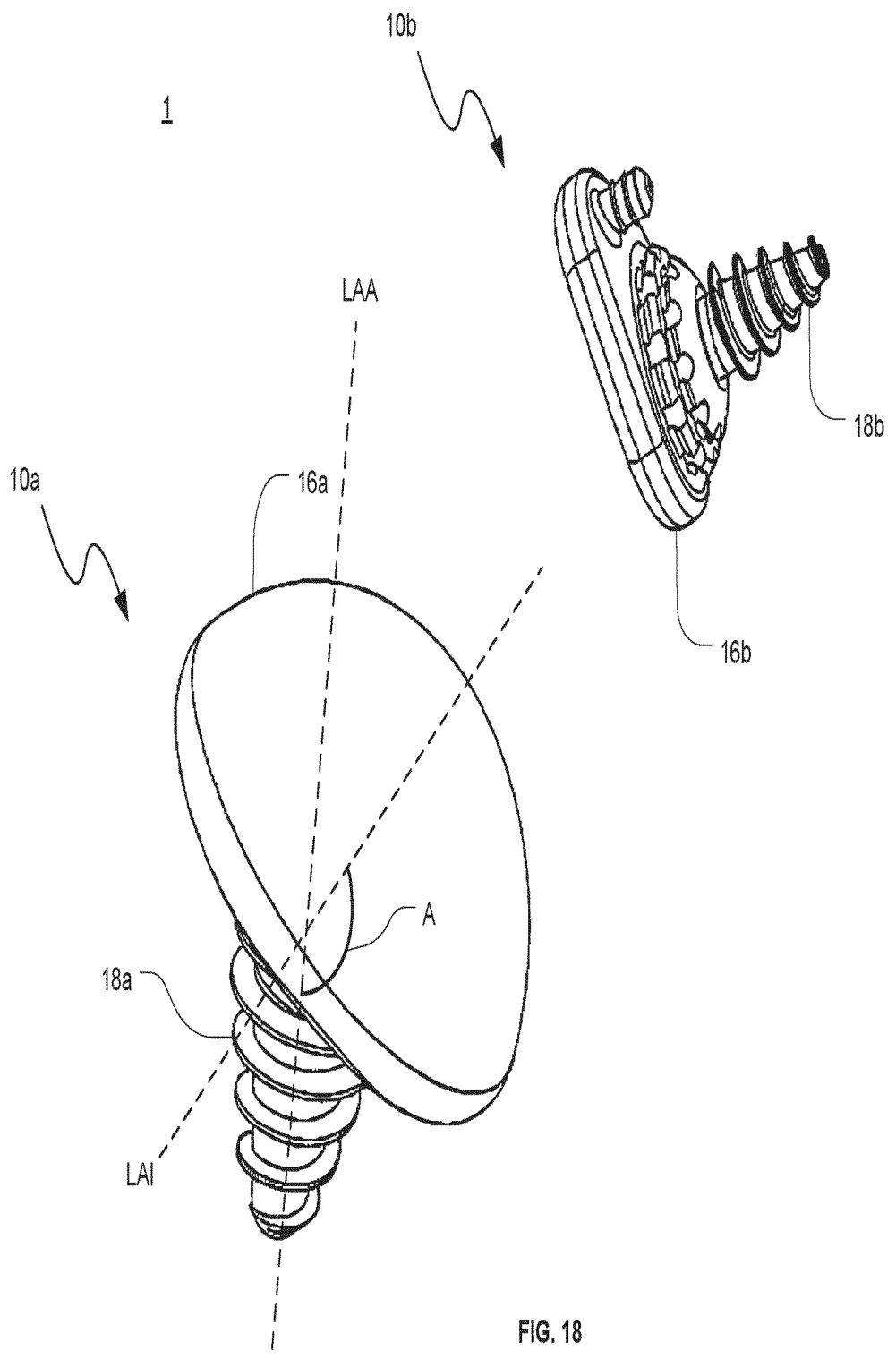
FIG. 18 generally illustrates yet another embodiment of an implant system which may be used with the total joint replacement system consistent with at least one embodiment of the present disclosure.

Turning now to FIG. 18, yet another embodiment of the total joint replacement system 1 consistent with the present disclosure is generally illustrated. The total joint replacement system 1 may include first implant system 10a and a second implant system 10b. While the total joint replacement system 1 will be described in terms of a shoulder joint, it should be appreciated that this is not, a limitation of the present disclosure unless specifically claimed as such. For the sake of clarity, the bones are not illustrated.

The first implant system 10a may be configured to replace and/or repair the humeral head, and may be similar to the implant system 10 described with respect to FIGS. 4 and 5-6. The implant 16a may include a first fixation element 32 configured to be secured to the second fixation element 44 of the anchor 18a as described herein (e.g., using one or more first fixation elements 32 configured to be secured to one or more second fixation elements 44). The anchor 18a may be secured, for example, into the humerus. The implant 16a may have a generally hemispherical configuration, for example, which generally corresponds to the humeral head (e.g., a "ball shape"). The implant 16a (e.g., the first fixation element 32) may be configured to be secured to the anchor 18a (e.g., the second fixation element 44) at any angle A. For example, the angle A may be defined by the longitudinal axis LAA of the anchor 18a and the longitudinal axis LAI of the implant 16a. The angle A may be determined based on the amount of the humeral head removed with respect to the rest of the humerus. The angle A may include any angle within the range of 0 degrees to approximately 90 degrees, for example, within the range of 0 degrees to approximately 45 degrees, within the range of 0 degrees to approximately 25 degrees, and/or within the range of 0 degrees to approximately 15 degrees, including all values and ranges therein.

The second implant system 10b may be configured to replace and/or repair the glenoid. The second implant system 10b may include any implant system/assembly as described in U.S. Provisional Application Ser. No. 61/949,789, filed Mar. 7, 2014, which is fully incorporated herein by reference.

Figure 19:
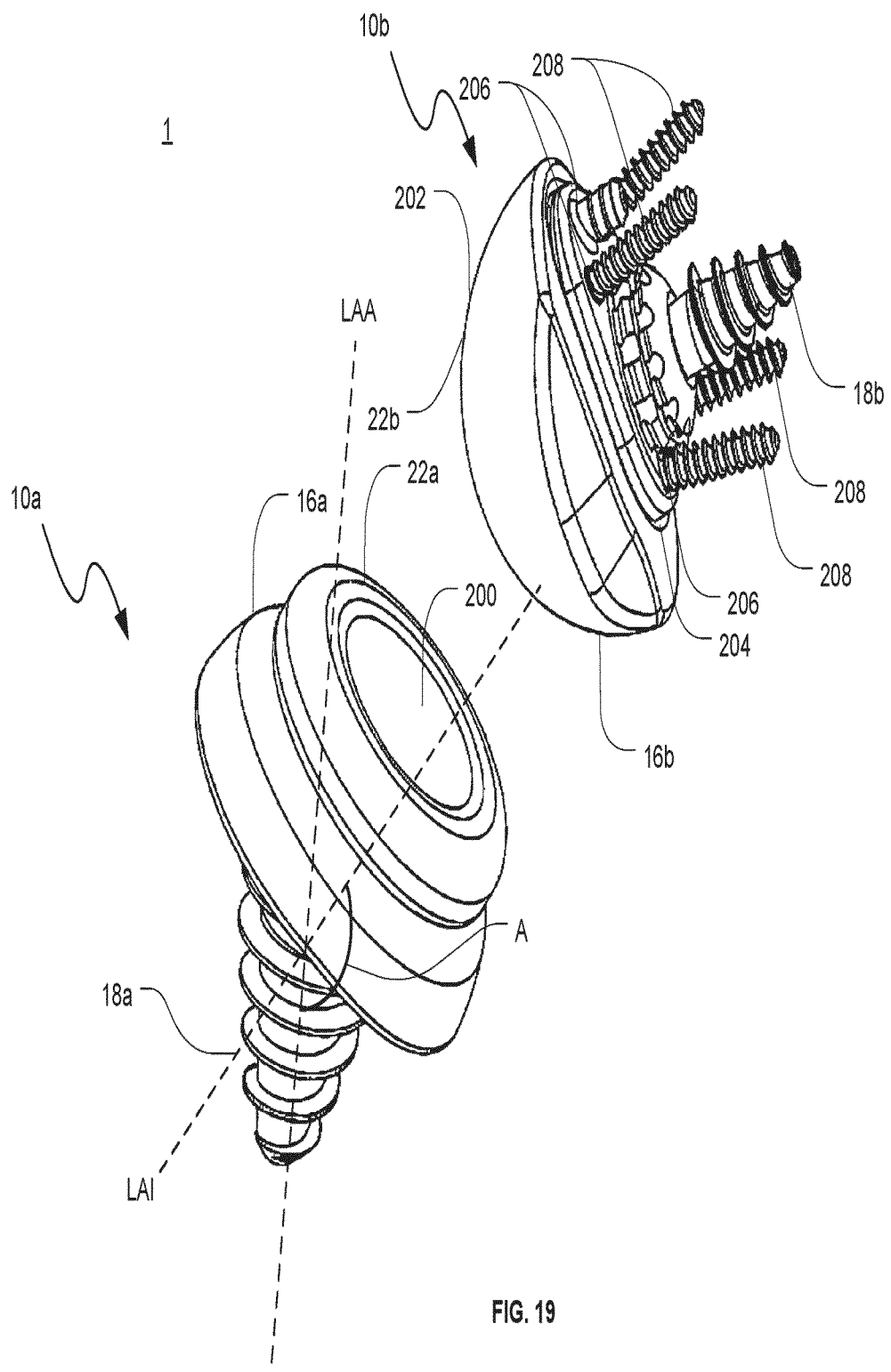
FIG. 19 generally illustrates a further embodiment of an implant system which may be used with the total joint replacement system consistent with at least one embodiment of the present disclosure.

The total joint replacement system 1 as generally illustrated in FIG. 18 may therefore repair and/or replace the shoulder joint. Turning now to FIG. 19, yet a further embodiment of the total joint replacement system 1 consistent with the present disclosure is generally illustrated. The total joint replacement system 1 of FIG. 19 may include first implant system 10a and a second implant system 10b, and may be used to repair and/or replace a shoulder joint (though it should be appreciated that this is not a limitation of the present disclosure unless specifically claimed as such). For the sake of clarity, the bones are not illustrated.

The total joint replacement system 1 may be referred to as a "reverse shoulder." The shoulder may be thought of as a ball and socket joint in which he humeral head is a ball and the glenoid is a socket. In the total joint replacement system 1 of FIG. 19, the orientation of the ball is socket is reversed. As such, implant system 10*a* (which may be secured to the humerus) may include an anchor 18*a* and an implant 16*a* having a load bearing surface 22 at least partially defining a socket 200. The implant 16*a* may be disposed at an angle A with respect to the anchor 18*a* as described herein.

The second implant system 10*b* may include an implant 16*b* and an anchor 18*b*. The implant 16*b* may be secured to the anchor 18*b* as generally described herein (e.g., using one or more first fixation elements 32 configured to be secured to one or more second fixation elements 44). The implant 16*b* may include an implant body 202 and a support plate 204. The implant body 202 may define a load bearing surface 22*b*, for example, having a generally hemi-spherical configuration (e.g., ball) configured to articulate in the socket 200 of the first implant system 10*a*. The implant body 202 may be secured to the support plate 204 in any manner known to those skilled in the art. For example, the implant body 202 may be secured to the support plate 204 using a tapered connection similar to the first and second fixation elements 32, 44 as described herein. The support plate 204 may optionally include one or more apertures 206 configured to receive anchoring screws 208. The anchoring screws 208 aid in securing the support plate 204 (and therefore the implant 18*b*) to the bone.

According to one embodiment, the total joint replacement system 1 of FIG. 18 may be partially replaced with the total joint replacement system 1 of FIG. 19. In particular, a patient may initially have the total joint replacement system 1 of FIG. 18 installed in the shoulder joint. If it is later desired to replace the total joint replacement system 1 of FIG. 18 with a reverse shoulder, the anchors 18*a*, 18*b* of FIG. 18 may remain secured within the humerus and glenoid, respectively. The implant 16*a*, 16*b* of FIG. 18 may be removed and replaced with the implants 16*a*, 16*b* of FIG. 19. Leaving the anchors 16*a*, 16*b* of FIG. 18 within the bones reduces the potential for damage to the bones if corrective surgery is later needed. As such, any of the implants 10 that may be used with the total joint replacement system 1 of the present disclosure may be considered modular.

In accordance with yet another embodiment of the present disclosure, an implant system is disclosed herein that allows for partial or total reconstruction of an articular surface of a bone. Suitable bones include, but are not limited to, humerus bones, femur bones, and/or any other bone type having an articular surface for forming a joint.

The implant system includes an anchor portion configured to be coupled to an implant portion. The anchor portion is configured to engage with/secure to the bone and the implant portion includes a load bearing surface that at least partially replaces the patient's articular surface. The anchor portion includes one or more anchor fixation heads configured to be at least partially received in a corresponding implant fixation cavity to couple the anchor portion with the implant portion. The anchor portion may be formed from a material (e.g., such as titanium, stainless steel, or another suitable metal/alloy) that is less dense than the material of the implant portion. The implant portion may be formed from a material (e.g., such as Cobalt-Chromium (CoCr) or other suitable material) that has a higher wear-resistance than the material of the anchor portion. As explained herein, the size and shape of the anchor fixation head and the implant fixation cavity, as well as the material selection of the anchor and implant portions, may reduce the overall weight of the implant system while still allowing the implant system to have excellent wear resistance.

It may be appreciated, however, that the anchor and implant portions may be formed from a same material (e.g., steel, titanium, Cobalt-Chromium or any other suitable metal/alloy), and this disclosure is not necessarily limited to an implant system having two different materials unless specifically claimed as such.

Figures 20, 21, 22:
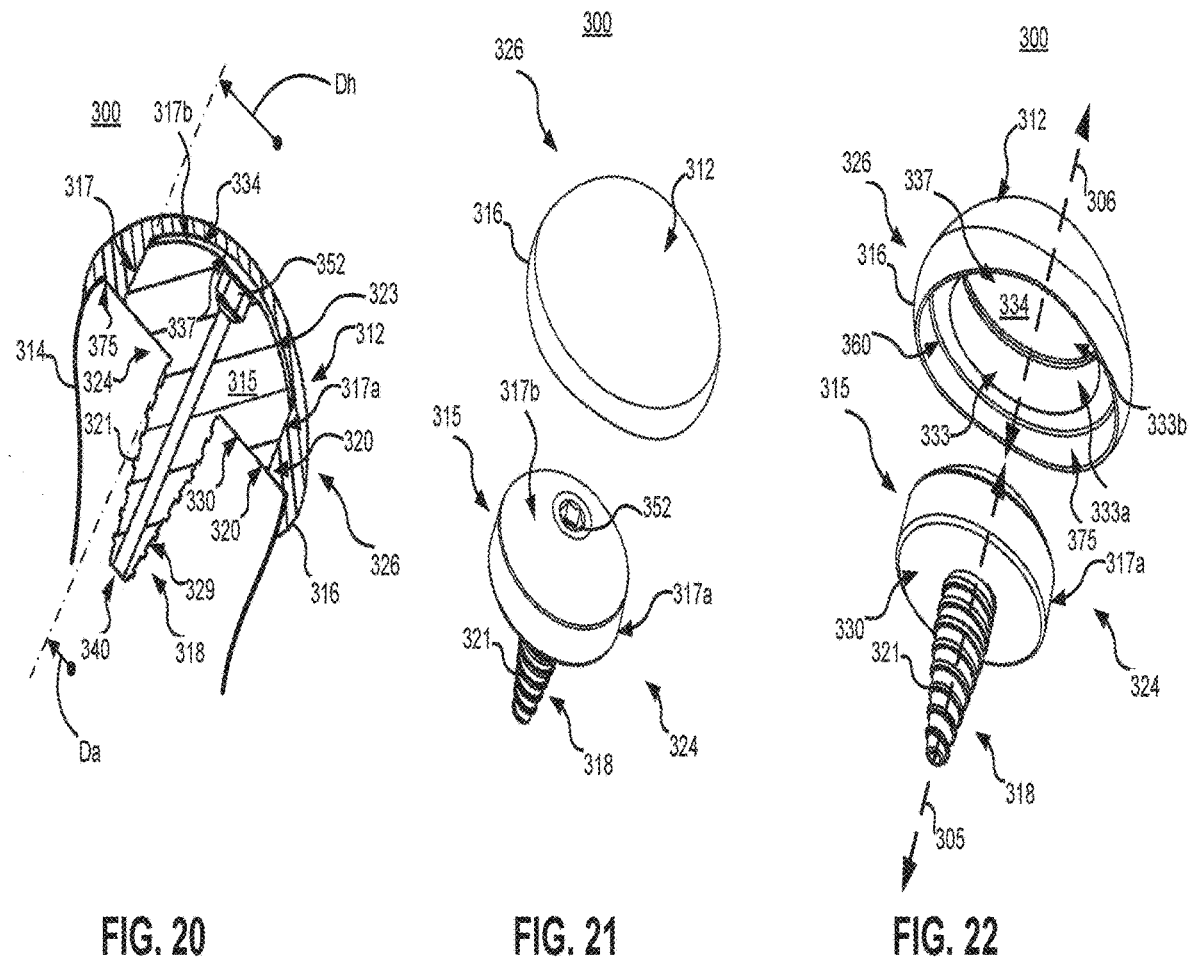
FIG. 20 generally illustrates an implant system installed in a patient's joint consistent with at least one embodiment of the present disclosure.
FIGS. 21 and 22 are perspective views that collectively illustrate the implant system of FIG. 20 in accordance with an embodiment of the present disclosure.

Turning now to FIG. 20, an embodiment of an implant system 300 (or joint replacement system 300) installed in a patient's humerus bone 314 (referred to herein as bone 314 for simplicity) is generally illustrated. While specific reference is made to a humerus bone in the proceeding aspects and examples, this disclosure is not limited in this regard and is equally applicable to other bones having articular surfaces/cartilage. The implant system 300 is configured to repair and/or replace a portion of or the entire articular surface of the humerus head of the humerus bone 314.

With reference to FIGS. 21-26, the implant system 300 includes an anchor portion 324 configured to be coupled to an implant portion 326. The anchor portion 324 (e.g., the anchor fixation head 315 and/or anchor 318) may optionally include a cannulated passageway 340 that extends from a first end to a second end generally along the longitudinal axis 305 of the anchor portion 324.

The anchor portion 324 includes an anchor fixation head 315 and an anchor 318. As used herein, the anchor 318 is defined as the part of the anchor portion 324 that is configured to be surrounded by the bone 314 beneath the excision site 320 when the anchor portion 324 is coupled/secured to the bone 314. At least a portion of the anchor 318 is also configured to engage with and/or secure the anchor portion 324 to the bone 314. According to one embodiment, the anchor 318 includes an elongated shaft/body 311, e.g., that may extend along the longitudinal axis 305 of the anchor portion 324. As used herein, the anchor fixation head 315 is defined as the part of the anchor portion 324 that is configured to be disposed external to (e.g., above) the bone 314 when the anchor portion 324 is coupled/secured to the bone 314 beneath the excision site 320.

The anchor portion 324 (e.g., the anchor fixation head 315 and the anchor 318) may be formed integrally from a single piece of material, e.g., as generally illustrated in FIGS. 21-26. Alternatively, the anchor portion 324 may be formed from two or more (e.g., via multiple pieces), which may be the same or different materials, e.g., as generally illustrated in FIG. 25. For example, the anchor fixation head 315 may be configured to be coupled to the anchor 318 in any manner known to those skilled in the art including, but not limited to, one or more friction connections 371 (e.g., a pair of Morse tapered mating surfaces), snap fit connections, and/or positive mechanical engagement connections.

With reference back to FIGS. 20-26, the anchor fixation head 315 includes an anchor bone facing surface 330 and an implant facing surface 323. The anchor fixation head 315 may be formed from a first material that is less dense than the implant portion 326 and suitable for use within implant devices. For example, the first material may comprise a metal such as titanium, steel, or other suitable metal/alloy. In some cases, the first material may be non-metal and formed from a ceramic, plastic and/or polymer. Note that the anchor fixation head 315 may not necessarily be formed from a light-weight (less dense) material depending on a desired configuration.

The anchor bone facing surface 330 extends generally radially outward from a first (e.g., proximal) end of the anchor 318 (e.g., the shaft/body 311) such that the anchor fixation head 315 has a cross-section that is greater than the cross-section of the anchor 318. According to one embodiment, at least a portion of the outer periphery of the anchor bone facing surface 330 (e.g., the entire outer periphery of the anchor bone facing surface 330) may extend radially outward a maximum radial distance Dh from a longitudinal axis 305 of the anchor 318 that is larger than the maximum radial distance Da of the outer periphery of the anchor 318 from the longitudinal axis 305.

The anchor bone facing surface 330 may optionally include a contour that substantially matches the resulting contour of the bone 314 within the excision site 320. For example, the anchor bone facing surface 330 may have a surface contour generally corresponding to the surface contour of the excision device revolved around the working axis used when forming the excision site 320. To this end, the anchor bone facing surface 330 may include a contour that is revolved around the longitudinal axis 305 of the anchor portion 324, and the bone facing surface 330 may directly contact the bone 314 within the excision site 320. It should be appreciated, however, that the bone-facing surface 330 may not necessarily directly contact the bone 314 and may include a gap (e.g., an air gap, or a gap comprising a be cement or other suitable adhesive) therebetween, depending on a desired configuration.

Figures 26, 27, 28:
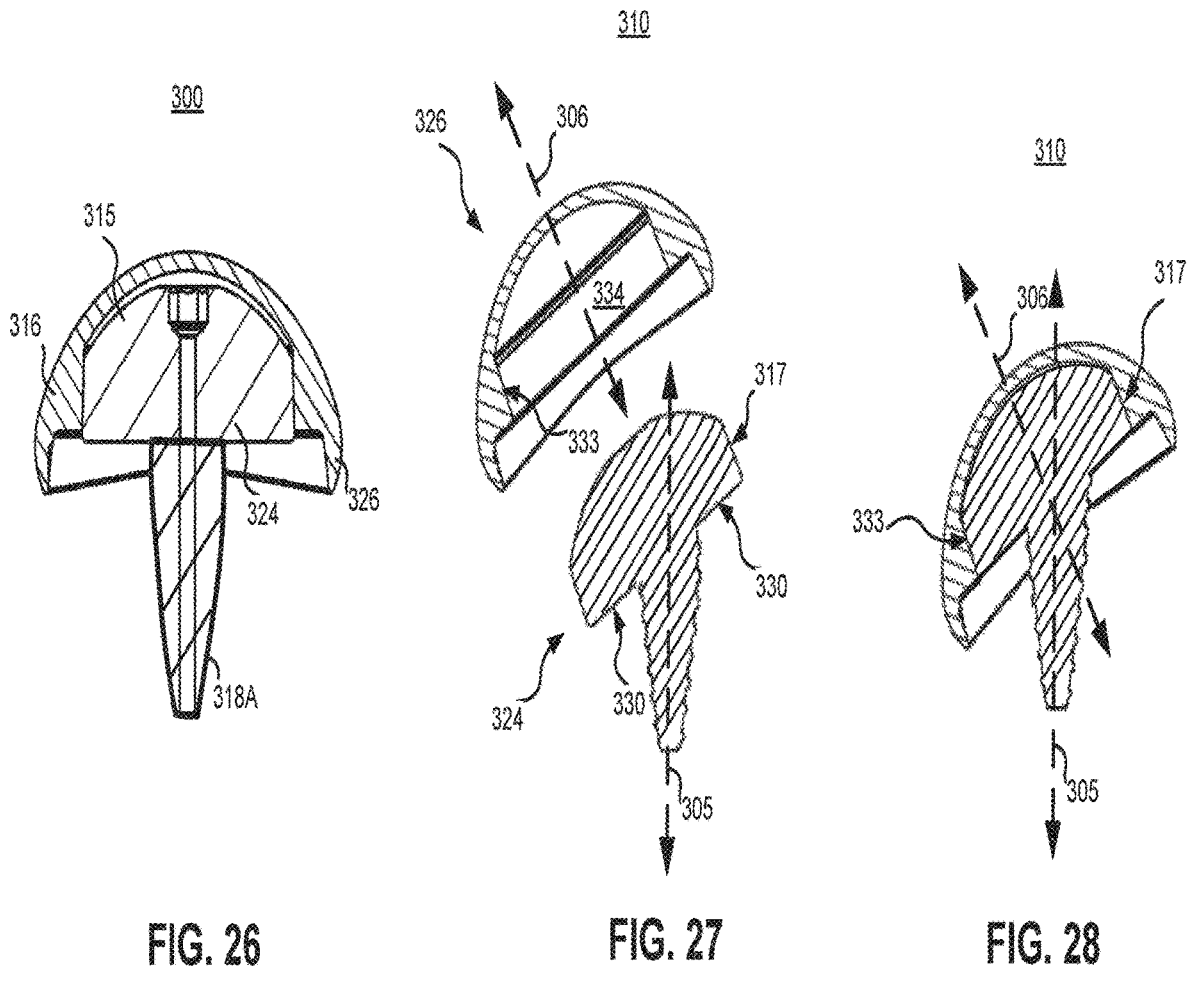
FIG. 26 generally illustrates a further embodiment of an implant system consistent with at least one embodiment of the present disclosure.
FIGS. 27-28 show an assembled and unassembled view of the implant system of FIG. 20, respectively, in accordance with an embodiment of the present disclosure.

In the illustrated embodiment, the anchor bone facing surface 330 extends generally perpendicularly radially outward from a first end of the anchor 318, though it should be appreciated that the anchor bone facing surface 330 may extend radially outward at an angle greater than and/or less than 90 degrees with respect to the longitudinal axis 305 of the anchor portion 324, e.g., as generally illustrated in FIGS. 27 and 28. As such, while the longitudinal axis 305 of the anchor portion 324 is illustrated in FIGS. 20-26 as being generally parallel or collinear with the central axis 306 of the implant portion 326, it should be appreciated that the anchor fixation head 315 may be configured to be coupled to the implant portion 326 such that the central axis 306 of the implant portion 326 intersects with the longitudinal axis 305 of the anchor portion 324 at a single point and the two axis 305, 306 are not, parallel or collinear to each other (e.g., as generally illustrated in FIGS. 27 and 28).

Referring back to FIGS. 20-26, the anchor fixation head 315 also includes an implant facing surface 323. The implant facing surface 323 is defined as a surface that is adjacent to (e.g., but not limited to, abutting) the anchor facing surface 337 of the fixation recess 334 when the anchor fixation head 315 is received within the fixation recess 334. At least a portion of the implant surface 330 may include one or more mating surfaces 317 for coupling to the implant portion 326 to the fixation recess/cavity 334 of the implant portion 326 (e.g., for coupling the mating surfaces 317 to one or more corresponding mating surfaces 333 of the anchor facing surface 337).

According to one embodiment, the mating surface 317 may include a tapered outer profile (e.g., a Morse taper or the like) configured to form a friction connection with a corresponding mating surface 333 (e.g., tapered mating surface) of the fixation recess 334 of the implant portion 326. For example, the anchor fixation head 315 may include, but is not limited to, a tapered semi-spherical or hemispherical ball shape such as shown. It should be appreciated, however, that the anchor fixation head 315 of the anchor portion 324 may be coupled to the fixation recess/cavity 334 of the implant portion 326 in any other manner such as, but not limited to, a snap fit connection, threaded connection, or the like.

The implant facing surface 323 (and optionally the mating surface 317) of the anchor fixation head 315 may extend from the periphery of the anchor bone facing surface 330 around all or a portion of the implant surface 330 of the anchor fixation head 315. For example, the mating surface 317 of the implant facing surface 323 may include a first portion 317a that extends substantially parallel with a longitudinal axis 305 of the anchor 318. In some cases, a second portion 317b of the mating surface 317 may also extend along substantially transverse relative to the longitudinal axis 305 of the anchor 318. The first portion 317a may directly contact a corresponding mating surface 333a of the implant portion 326 when the anchor portion 324 is received in the fixation recess 334, for example to form a frictional connection therebetween. Alternatively (or in addition), the second portion 317b may directly contact a corresponding mating surface 333b of the implant portion 326 when the anchor portion 324 is received in the fixation cavity/recess 334 (e.g., to form a frictional connection therebetween), although other embodiments are within the scope of this disclosure.

Thus, it should be appreciated that all or a portion of the implant facing surface 323 may form the mating surface 317. In at least one embodiment, a gap (e.g., an air gap) may be formed between the portion of the implant facing surface 323 and the anchor facing surface 337 of the fixation recess 334, e.g., as generally illustrated in FIG. 20. While the mating surface 317 is shown extending from the periphery of the anchor bone facing surface 330, it should be appreciated that the present disclosure is not limited to this configuration, and the mating surface 317 may not extend from the periphery of the anchor bone facing surface 330.

As noted above, the implant facing surface 323 of the anchor fixation head 315 may have a generally hemispherical configuration configured to be received in a corresponding generally hemispherical fixation cavity/recess 334 of the implant portion 326 as described in more detail herein. One benefit to this configuration is that the anchor portion 324 may be rotated within the bone 314 to adjust the height of the anchor fixation head 315 (and thus the resulting height of the implant portion 326) relative to the bone 314/patient's articular surface without affecting the orientation of the implant portion 326 relative to the patient's original articular surface when the implant portion 326 is coupled to the anchor portion 324.

According to another embodiment, the anchor fixation head 315 may have a non-circular cross-section, e.g., as shown in FIGS. 30-32, configured to be received in a corresponding non-circular cross-sectional cavity/recess 334. One benefit to this configuration is that the anchor portion 324 cannot rotate relative to the implant portion 326 when the implant portion 326 is coupled to the anchor portion 324.

As noted herein, the anchor 318 refers to the part of the anchor portion 324 that is configured to be surrounded by the bone 314 beneath the excision site 320 when the anchor portion 324 is coupled/secured to the bone 314. At least a portion of the anchor 318 is also configured to engage with and/or secure the anchor portion 324 to the bone 314. According to one embodiment, the anchor 318 includes an elongated shaft/body 311, e.g., that may extend along the longitudinal axis 305 of the anchor portion 324.

According to one embodiment, the anchor 318 may include one or more threads 321 (which may be either continuous or discontinuous threads), ribs, rings, protrusions, barbs, bone-ingrowth materials (e.g., a bone-ingrowth matrix material. e.g., as generally illustrated in FIG. 26), or the like, which may extend along all and/or a portion of the shaft 311 of the anchor 318. The use of threads 321 as generally illustrated may advantageously allow the height of the anchor portion 324 (e.g., the anchor fixation head 315) to be adjusted relative to the excision site 320/articular surface by rotating the anchor 318 within the bone 314. For example, the anchor 318 may be rotated such that the anchor fixation head 324 (e.g., the bone facing surface 330) is flush with and/or abuts against the surface of the bone 314 within the excision site 320 (i.e., such that the anchor fixation head 315 is external to/above the bone 314 and the anchor 318 is surrounded by the bone 314).

As noted above, however, the anchor 318 does not have to include threads, and may be secured to the bone 314 in any manner know to those skilled in the art. For example, the anchor 318 may form a non-circular cross-sectional peg that may be pressed into (e.g., driven and/or pounded into) the bone 314 within the excision site 320 and/or may include one or more ribs, rings, protrusions, barbs, bone-ingrowth materials (e.g., bone-ingrowth matrix material, e.g., as generally illustrated in FIG. 26), or the like. Optionally, the anchor 318 may be secured to the bone 314/excision site 320 using bone cement.

The implant portion 326 includes an implant body 316 defining one or more fixation cavities/recesses 334, a load bearing surface 312 having a contour for articulating against an articulating surface (e.g., a load bearing surface and/or articular surface of the cooperating/corresponding bone of the joint), and optionally an implant bone-facing surface 375 disposed opposite the load bearing surface 312.

According to one embodiment, the implant portion 326 may form a generally hemispherical ball shaped load bearing surface 312 configured to articulate, at least in part, in a socket (such as, but not limited to, a glenoid fossa or other joint); however, the shape of the load bearing surface 312 may depend on the intended application. For instance, the articular surface 312 may include one or more concave regions.

The load bearing surface 312 may have a contour that substantially matches and/or is based on the contours of the patient's original articular surface that is removed when forming the excision site 320. The contour of the load bearing surface 312 may be based on a plurality of measurements taken at the patient's articular surface (for example, using a measuring and/or mapping tool as generally described in U.S. Pat. Nos. 6,520,964, 6,610,067, 6,679,917, 7,029,479 and 7,510,558, which are fully incorporated herein by reference) and/or may be based on one or more templates. The load bearing surface 312 may be based on two or more curvatures, for example, the anterior-posterior curvature and the superior-inferior curvature. One or more of the anterior-posterior and/or superior-inferior curvatures may themselves be based on multiple curves. (for example, as generally described in U.S. patent application Ser. No. 12/027,121, filed Feb. 6, 2008 and entitled System and Method for Joint Resurface Repair, which is fully incorporated herein by reference).

Alternatively, in the case of a total joint replacement in a ball and socket type joint (e.g., shoulder), the load bearing surfaces may be reversed (i.e., the load bearing surface 312 of the implant portion 326 which is secured in the humeral head may form a socket shaped load bearing surface 312 and the glenoid implant (not shown) may form a ball shaped load bearing surface), for example, as generally described in FIGS. 18 and 19. As such, the load bearing surface 312 may not substantially match and/or be based on the contours of the patient's original articular surface that is removed when forming the excision site 320.

The implant portion 326 may be formed from a single piece of material or formed via multiple pieces (which may be the same or different materials). The implant portion 326 may be formed from a second material that has a higher wear-resistance and/or higher density compared to the material of the anchor portion 324. For example, the implant portion 326 may be formed of a material having an absolute density of greater than 5 g/cm³, for example, greater than 8 g/cm³. In at least one embodiment, the implant portion 326 may be formed from cobalt-chromium (CoCr) and/or CoCr alloys, although the present disclosure is not limited to CoCr and other materials are within the scope of this disclosure. In some cases, the implant portion 326 may include a material (e.g., but not limited to, CoCr/CoCr alloy) having a hardness ranging from a greater than 500 MPa (e.g., 550-800 MPa) and/or a tensile strength greater than 145 MPA (e.g., 145-270 MPa). The CoCr alloy may optionally include nickel, carbon, and/or nitrogen to stabilize the 7 phase in order to further increase ductility and reduce occurrences of component fracture. Additionally, the second material may be non-metal and formed from a ceramic, plastic and/or polymer. In at least one embodiment, the implant portion 326 may include an outer layer of a second material that at least partially covers/surrounds a core material (e.g., forming a body that defines the implant fixation cavity 334), wherein the second material has a higher wear-resistance and/or higher density compared to the core material.

The implant body 316 further provides a fixation recess 334 (also be referred to as a fixation receptacle or cavity), which is more clearly shown in FIGS. 22 and 23. The fixation recess 334 includes an anchor facing surface 337 that is disposed within an opening 360. At least a portion of the anchor facing surface 337 of the fixation recess 334 includes one or more mating surface 333 for coupling to the corresponding mating surface 317 of the anchor portion 324. For example, the mating surface 333 may include a tapered outer profile (e.g., a Morse taper or the like) configured to form a friction connection with a corresponding mating surface 317 (e.g., tapered mating surface) of the anchor fixation head 315 of the anchor portion 324. In at least one embodiment, the fixation recess 334 may include, but is not limited to, a tapered semi-spherical or hemispherical recess shape such as shown. It should be appreciated, however, that the fixation recess 334 of the implant portion 326 may be coupled to the anchor fixation head 315 of the anchor portion 324 in any other manner such as, but not limited to, a snap fit connection, threaded connection, or the like.

According to one embodiment, the mating surface 333 of the implant portion 326 may extend from the periphery of the opening 360 of the implant portion 326. In addition (or alternatively), the mating surface 333 of the implant portion 326 may extend from the periphery of a bone facing surface 375 of the implant portion 326. In either case, the mating surface 333 may extend around all or a portion of the inner surface of the fixation recess 334. For example, the mating surface 333 may include a first portion 333a that extends substantially parallel with a longitudinal axis 306 of the implant portion 326. The first portion of the mating surface 333a may frictional engage with the first portion 317a of the anchor fixation head 315. Alternatively (or in addition), a second portion 333b of the mating surface 333 may extend along substantially transverse relative to the longitudinal axis 306 of the implant portion 326, and may optionally frictionally engage with the second portion 317b of the anchor fixation head 315 (though it should be appreciated that a gap (e.g., an air gap) may be formed between the mating surface 317 of the anchor fixation head 315 and the mating surface 333 of the fixation cavity/recess 334, e.g., such as shown in FIG. 20). While the mating surface 333 is shown extending from the periphery of the bone facing surface 375 (i.e., from the opening 60), it should be appreciated that the present disclosure is not limited to this configuration, and the mating surface 333 may not extend from the periphery of the anchor bone facing surface 375 and may form only a portion of the anchor facing surface 337.

The implant bone-facing surface 375 may overlap a portion of the bone 314 to fully cover/surround the anchor fixation head 315 of the anchor portion 324 and a portion of the bone 314. The implant bone facing surface 375 may optionally include a contour that substantially matches the resulting contour of the bone 314 within the excision site 320. For example, the implant bone facing surface 375 may have a surface contour generally corresponding to the surface contour of the excision device revolved around the working axis used when forming the excision site 320. To this end, the implant bone facing surface 375 may include a contour that is revolved around the longitudinal axis 306 of the implant portion 326, and the implant bone facing surface 375 may directly contact the bone 314 within the excision site 320. In one embodiment, the implant bone facing surface 375 extends from the opening 360 of the fixation cavity 334, though this is a not a limitation of the present disclosure unless specifically claimed as such. All or a portion of the implant bone facing surface 375 may directly contact the bone 314. Alternatively, all or a portion of the implant bone facing surface 375 may be separated from the bone 314, for example, by way of a gap. The gap may be optionally at least partially filled with bone cement or the like.

As may be appreciated, the load bearing surface 312 of the implant portion 326 may be constructed from a material having a high wear resistance such that the implant system 300 does not prematurely wear out during use. One disadvantage to many high wear resistant materials (e.g., but not limited to, CoCr) is that they are typically very dense, and as a result, the weight of the implant system 300 may become a factor as the surface area of the load bearing surface 312 increases.

As noted herein, the size and shape of the anchor fixation head 315 and the implant fixation cavity 334, as well as the material selection of the anchor portion 324 and implant portion 326, may reduce the overall weight of the implant system 300 while still allowing the implant system 300 to have excellent wear resistance and structural strength. In particular, the anchor portion 324 includes an anchor fixation head 315 that is constructed from a material that is less dense than the material of the implant portion 326 while also providing support for the implant portion 326 (thereby ensuring that the implant portion 324 does not distort when exposed to stress/forces during use). As a result, the amount of high wear resistant material used to form the implant portion 326 may be significantly reduced because the anchor portion 324 (e.g., the anchor fixation head 315) may occupy a greater volume of the implant system 300.

For example, as best shown in FIG. 23, the fixation recess 334 may define a volume Vr that is greater than or equal to 50% of the total volume Vi of the implant portion 326. As used herein, the volume Vr of the fixation recess 334 is defined as the volume of the fixation recess 334 between the opening 360 of the fixation recess 334 and the anchor facing surface 337 of the fixation recess 334. Additionally, as used herein, the total volume Vi of the implant portion 326 is defined as displacement volume of the implant portion 326. For example, the volume Vr of the fixation recess 334 may be greater than or equal to 60% of the total volume Vi of the implant portion 326, the volume Vr of the fixation recess 334 may be greater than or equal to 70% of the total volume Vi of the implant portion 326, and/or the volume Vr of the fixation recess 334 may be greater than or equal to 80% of the total volume Vi of the implant portion 326, including all values and ranges therein.

Similarly, the anchor fixation head 315 may define a volume Vh that is greater than or equal to 50% of the total volume Vi of the implant portion 326. As used herein, the volume Vh of the anchor fixation head 315 is defined as the volume of the anchor portion 324 that is configured to be disposed external to (e.g., above) the bone 314 when the anchor portion 324 is coupled/secured to the bone 314 beneath the excision site 320. For example, the volume Vh of the anchor fixation head 315 may be greater than or equal to 60% of the total volume Vi of the implant portion 326, the volume Vh of the anchor fixation head 315 may be greater than or equal to 70% of the total volume Vi of the implant portion 326, and/or the volume Vh of the anchor fixation head 315 may be greater than or equal to 80% of the total volume Vi of the implant portion 326, including all values and ranges therein.

The opening 360 of the fixation recess 334 may have a cross-section that is greater than the cross-section of the anchor 318. According to one embodiment, the opening 360 may extend radially outward a maximum radial distance Do from a longitudinal axis 306 of the anchor portion 326 that is larger than the maximum radial distance Da of the anchor 318. For example, the opening 326 and the anchor 318 may have circular cross-sections, and maximum radial distance Do (e.g., diameter) may be larger than maximum radial distance Do (e.g., diameter Da), though it should be appreciated that the opening 360 and/or anchor 318 may have non-circular cross-sections. The maximum radial dimension Do of the opening 360 may also be approximately equal to the maximum radial dimension Dh of the implant fixation head 315 (e.g., such that a frictional connection may be formed therebetween).

The maximum radial dimension Do of the opening 360 may be greater than 50% and less than 95% of the maximum radial dimension Di of the implant portion 326. For example, the maximum radial dimension Do of the opening 360 may be greater than 60% and less than 95% of the maximum radial dimension Di, the maximum radial dimension Do of the opening 360 may be greater than 70% and less than 95% of the maximum radial dimension Di. and/or the maximum radial dimension Do of the opening 360 may be greater than 80% and less than 95% of the maximum radial dimension Di, including all values and ranges therein.

Figure 29:
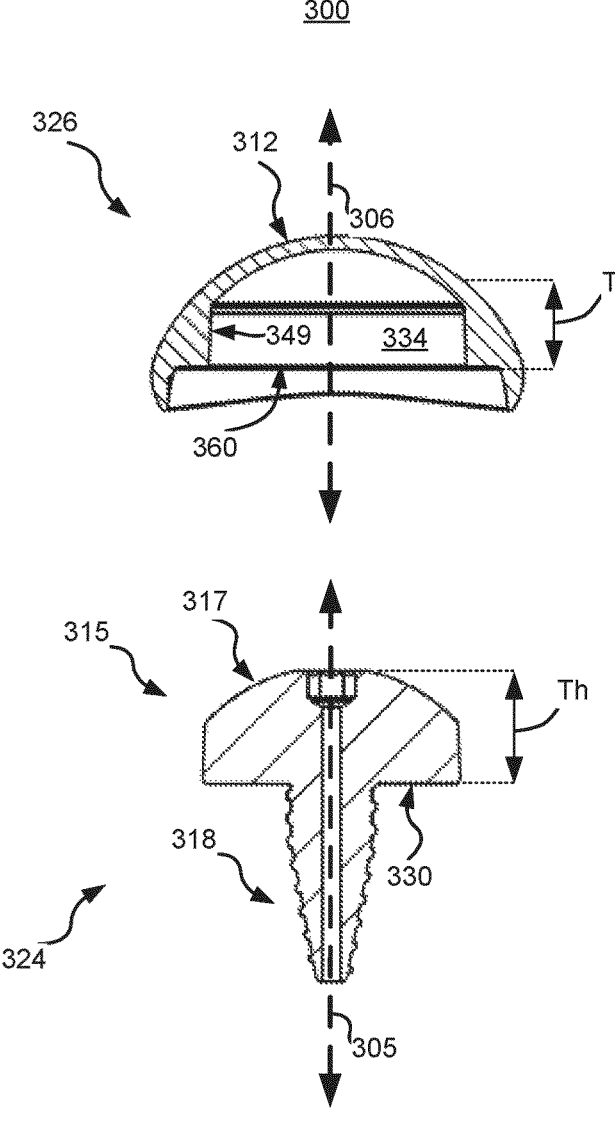
FIG. 29 shows another cross-sectional view of another embodiment of the implant system of FIG. 20.

In at least one embodiment, the maximum thickness Ti of the implant portion 326 is less than the maximum thickness Th of the anchor fixation head 15, such as shown in FIG. 29. As used herein, the maximum thickness Ti of the implant portion 326 is defined as the maximum thickness (e.g., distance) of the implant portion 326 between opposing sides of load bearing surface 312 and the inner surface 349 of the fixation cavity 334 taken parallel to the longitudinal axis 306 of the implant portion 326. Additionally, as used herein, the maximum thickness Th of the anchor fixation head 315 is defined as the maximum thickness (e.g., distance) of the anchor fixation head 315 between opposing sides of bone facing surface 312 and the mating surface 317 of the anchor fixation head 315 taken parallel to the longitudinal axis 305 of the anchor portion 324. For example, the maximum thickness Ti of the implant portion 326 may be less than or equal to 50% of the maximum thickness Th of the anchor fixation head 315, the maximum thickness Ti of the implant portion 326 may be less than or equal to 40% of the maximum thickness Th of the anchor fixation head 315, the maximum thickness Ti of the implant portion 326 may be less than or equal to 30% of the maximum thickness Th of the anchor fixation head 315, the maximum thickness Ti of the implant portion 326 may be less than or equal to 20% of the maximum thickness Th of the anchor fixation head 315, and/or the maximum thickness Ti of the implant portion 326 may be less than or equal to 10% of the maximum thickness Th of the anchor fixation head 315, including all values and ranges therein.

The anchor portion 324 may include a driving feature, e.g., driving receptacle 352, configured to engage with a driver (e.g., a drill or other suitable apparatus) to rotate and drive the anchor 318 into the bone 314 (e.g., a pre-drilled opening 329 of FIG. 20) to bring the bone-facing surface 330 into proximity and/or contact with excision site 320. Alternatively. or in addition to the driving receptacle 352, the anchor portion 324 (e.g., the outer periphery of the anchor bone facing surface 330) may include contours that allow for driving the anchor portion 324 by providing surfaces that may be engaged with a tool/apparatus having a corresponding shape. For example. FIGS. 30-32 illustrate top-down plan views showing example configurations for the anchor portion 324. FIG. 30 shows the outer periphery of the anchor bone facing surface 330 having a hexagonal shape to provide sidewalls for engaging a corresponding tool. Likewise. FIG. 31 shows the outer periphery of the anchor bone facing surface 330 having a triangular shape. FIC, 32 shows the outer periphery of the anchor bone facing surface 330 having a generally rectangular or square shape. Other regular and irregular shapes are also within the scope of this disclosure.

The excision site 320 may be formed using any method and system known to those skilled in the art, such as, but not limited to, as the systems and methods as described in U.S. Pat. Nos. 6,520,964, 6,610,067, 6,679,917, 7,678,151, 7,896,883, 8,177,841, and 8,388,624, as well as U.S. Publication No. 2010/0368238, all of which are fully incorporated herein by reference. As noted herein, the anchor 318 may optionally include a passageway 340, for example, a longitudinal passageway, configured to be advanced over a guide wire (not shown) as generally described in U.S. Pat. Nos. 6,520,964, 6,610,067, 6,679,917, 7,678,151, 7,896, 883, 8,177,841, and 8,388,624, as well as U.S. Publication No. 2010/0368238, all of which are fully incorporated herein by reference. For example, the anchor 318 may be inserted into bone 314 or may be inserted into a shaft drilled in the bone 314 to reduce risks or complications arising from the insertion of the anchor 318. Without limitation, a pilot hole may be formed in the bone 314 for receiving the anchor 318 prior to installing the anchor 318. A diameter of the pilot hole may be smaller than the anchor 318, although example embodiments may vary and are not limited thereto.

Once the anchor portion 324 has been secured to the bone 314, the implant portion 326 may then be coupled to the anchor portion 324. A region of the implant body 316 of the implant portion 326 (e.g., bone-facing surface 375) may overlap the bone 314 to fully cover/surround the anchor fixation head 315 of the anchor portion 324 and a portion of the bone 314. The implant portion 326 may be attached to the anchor portion 324 via a friction fit, adhesive, and/or any other suitable fixation approach.

Figures 33, 34, 35:
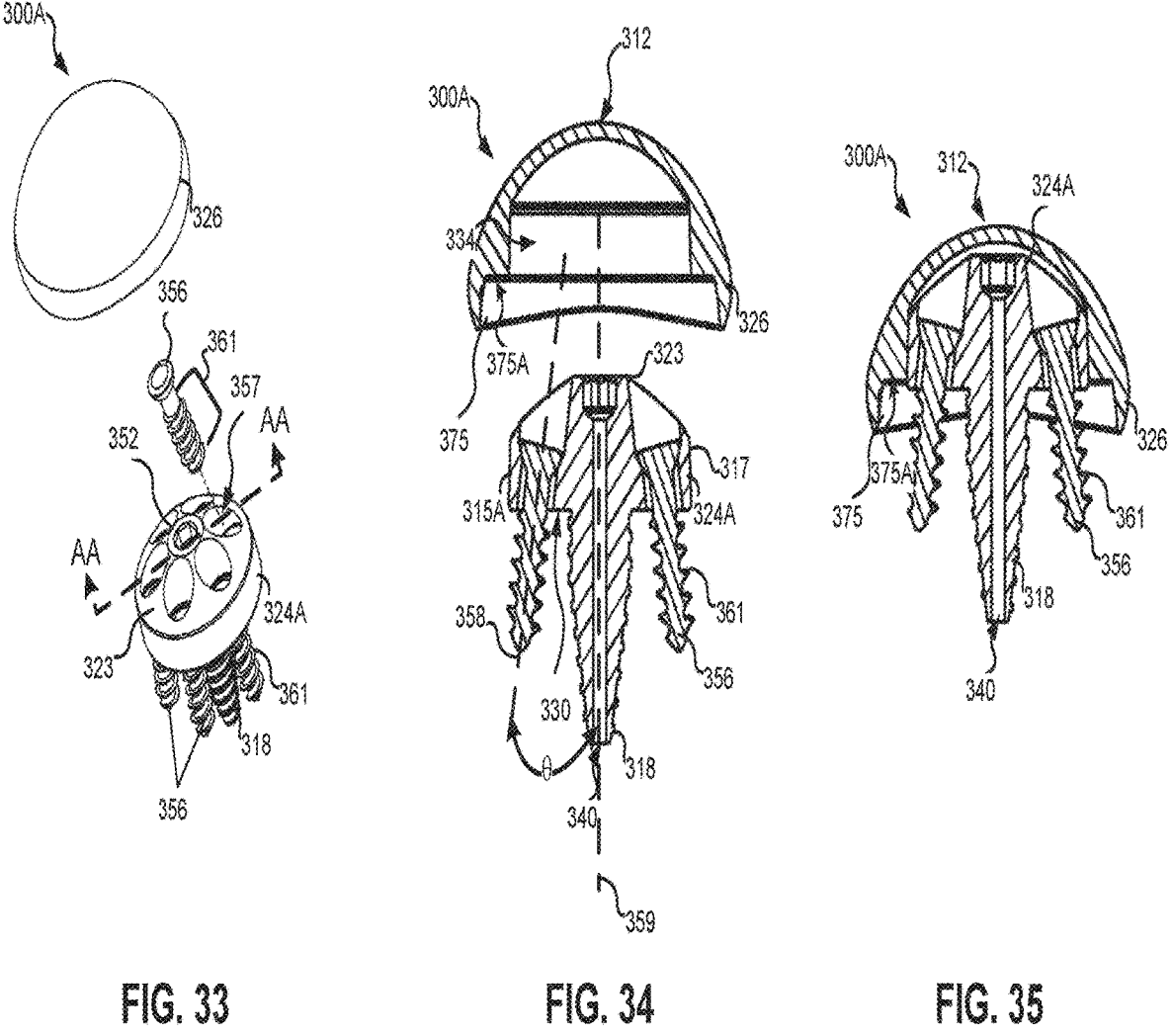
FIG. 33 generally illustrates a further example of an implant system consistent with at least one embodiment of the present disclosure.
FIGS. 34 and 35 show an assembled and unassembled view of the implant system of FIG. 33, respectively, in accordance with an embodiment of the present disclosure.

Turning now to FIGS. 33-35, yet another embodiment of an implant system 300A consistent with the present disclosure is generally illustrated. As shown, the implant system

300A is substantially similar to the implant system 300 of any one of FIGS. 20-29 and may include an anchor portion 324A and an implant portion 326. Accordingly, the permutations and variations discussed in the proceeding description are equally applicable to the implant system 300A and will not be repeated for the sake of brevity. However, as further shown, the embodiment of the implant system 300A illustrated in FIGS. 33-35 further includes the anchor portion 324A having a plurality of fixation members 356 configured to extend at least partially through and/or around the anchor portion 324A to further secure the implant system 300A to a bone. e.g., the bone 314, which will now be discussed in greater detail.

The anchor portion 324A includes a plurality of fixation member openings 357, which may be disposed adjacent the driving receptacle 352 and the anchor 318. The plurality of fixation member openings 357 may extend through anchor fixation head 315. For example, the fixation member openings 357 may extend from the implant facing surface 323 of the anchor fixation head 315, through a portion of the anchor fixation head 315, to the bone facing surface 330. The fixation member openings 357 may be spaced evenly apart from each other and, for instance, the driving receptacle 352 and the anchor 318.

As shown more clearly in FIG. 34, each of the plurality of fixation member openings 357 may include an opening having a longitudinal axis 358 that is offset by an angle θ relative to a longitudinal axis 359 of the anchor portion 324A, or more specifically anchor 318, with angle θ being about 45 degrees±10 degrees. In some cases, angle θ may measure between 0 degrees to 50 degrees depending on a desired configuration. Other spacing configurations and angles may be utilized and the particular configuration shown is not intended to be limiting. Moreover, although six (6) fixation members 356 and associated fixation member openings 357 are shown, this should not be construed as limiting. For example, the anchor portion 324A may include less fixation members. e.g., a single fixation member 356 and associated opening 357, or may include a greater number of fixation members (e.g., more than six).

Each of the fixation members 356, which may also be referred to as secondary anchors, may comprise a screw, peg, nail, or other suitable type of fastening device. Each of the fixation members 356 may include threads 361, although this disclosure is not limited in this regard. Each fixation member may be secured to the bone 314, for example, using one or more external threads, ribs, protrusions, bone cement, barbs, grooves or any other suitable structure that enables the same to be secured to the bone 314. Note that in some cases each of the fixation members 356 may not necessarily include threads 361 and may form peg-like structures, similar to that of the anchor 318A shown in FIG. 26.

Each fixation member 356 may include a tapered shape whereby a head portion includes a width larger than the shaft portion in order to allow a driving device. e.g., a driving bit, to be inserted into a receptacle of the head portion to allow each fixation member 356 to be driven into a bone, e.g., a bone 314, to form a frictional connection therebetween. In some cases, the shaft of each fixation member 356 includes a tapered shape as well, similar to that of the anchor 318. In some cases, each of the fixation openings 357 may include a width that is slightly larger than each head portion to allow each fixation member 356 to be counter-sunk into the anchor fixation head 315A of the anchor portion 324A, such as shown.

However, other embodiments arm within the scope of this disclosure and each fixation member 356 may not necessarily be countersunk into the anchor fixation head 315A. As generally referred to herein, countersunk generally refers to the head/driving portion of a fixation member 356 being disposed beneath the implant facing surface 323. To this end, each of the fixation member openings 357 may comprise a tapered recess which, in a general sense, acts as a stop to prevent an associated fixation member 356 from traveling beyond a certain point within the anchor fixation head 315A. Thus, each fixation member 356 may securely couple to the anchor fixation head 315 at a first end and within an associated fixation recess of the bone 314 (not shown) at the other end. Stated differently, the tapered shape of each fixation member opening 357 may result in each fixation member 356 forming a tapered connection with an associated fixation member opening 357 when inserted into the same.

FIG. 34 generally illustrates a cross-sectional view of one embodiment of an exploded, unassembled implant system 300A taken along the line A-A of FIG. 33, and FIG. 35 generally illustrates a cross-sectional view of the assembled implant system 300A also taken along the line A-A of FIG. 33. As shown, the anchor portion 324A includes a mating surface 317 and the implant portion 326 includes a fixation recess 334 for receiving at least a portion of the anchor portion 324A and coupling to the mating surface 317, via a frictional connection for example.

The implant system 300A may be attached to an excision site (not shown) in a manner similar to that of excision site 320 as described above with regard to any of the implant systems 300 of FIGS. 21-26.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the an. The present disclosure should, therefore, be considered to encompass such combinations, variations, and modifications.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined. i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

What is claimed is:

1. A method for inserting an implant assembly into a bone, the implant assembly comprising i) an anchor, ii) an implant having an anchor facing surface configured to interface with the anchor so as to couple therewith, and a load bearing surface, the method comprising:

securing a suture to the anchor, wherein a portion of the suture between a first and second end thereof engages with a contact portion of the anchor;

engaging a distal end of a driver shaft of a driver with an anchor engagement portion located at a proximal end of the anchor;

securing engagement between the driver and the anchor by applying tension to the suture;

inserting the anchor into the bone via the driver;

decoupling the driver from the anchor after the anchor is inserted into the bone;

engaging the anchor facing surface of the implant with the anchor;

securing the first and second ends of the suture to the driver shaft, the driver shaft being spaced apart from the implant;

coupling the driver shaft with a biasing member at a proximal end thereof, such that at least a portion of the biasing member is disposed between the driver shaft and the implant; and reducing a length of the suture extending between the anchor and the driver shaft, such that a distal end of the biasing member interfaces with the implant and provides a biasing force thereto so as to secure the implant to the anchor; wherein the anchor further comprises an anchor fixation portion configured to couple a proximal end of the anchor to the distal end of the biasing member.

2. The method of claim 1, wherein the anchor engagement portion further comprises a driver receptacle disposed at least partially within the anchor and configured to receive a driver engagement member of the driver.

3. The method of claim 1, further comprising removably coupling the distal end of the biasing member to the anchor fixation portion.

4. The method of claim 1, wherein the anchor further comprises a cannulated passageway disposed through a longitudinal axis of the anchor; and wherein the driver further comprises a longitudinal passageway disposed through a longitudinal axis of the driver shaft.

5. The method of claim 4, further comprising:

inserting a guide wire to abut the bone or at least be partially disposed in an excision site at the bone;

advancing the anchor over the guide wire such that the guide wire is at least partially disposed within the cannulated passageway, so as to align the anchor with the excision site;

advancing the driver over the guide wire such that the guide wire is at least partially disposed within the longitudinal passageway; and removing the guide wire.

6. The method of claim 1, further comprising removing at least a portion of the suture from the anchor.

7. The method of claim 6, wherein the suture is removed by pulling the first end of the suture such that the second end of the suture travels through the implant assembly and is removed therefrom.

8. The method of claim 1, wherein the contact portion of the anchor is selected from a group consisting of one or more of a flat edge, a guide, a slot, a channel, or any combination thereof.

9. The method of claim 1, further comprising wrapping at least a section of the suture around the anchor such as to form a basket or a loop.

10. The method of claim 1, wherein the biasing member further comprises at least one suture alignment guide configured to retain the suture about the biasing member.

11. The method of claim 1, wherein the driver shaft further comprises a suture engagement portion configured to secure the suture thereto.

12. The method of claim 11, further comprising passing at least a region of the suture through a region of the suture engagement portion comprising an aperture disposed through the driver shaft.

13. The method of claim 1, further comprising passing the first and second ends of the suture through first and second windows disposed through an outer surface of the biasing member to a biasing member passageway disposed through a longitudinal axis of the biasing member.

14. The method of claim 1, wherein coupling the driver shaft with the biasing member comprises positioning a longitudinal axis of the driver shaft generally perpendicular to a longitudinal axis of the biasing member, such that the driver shaft interfaces with a driver cradle at least partially disposed at the proximal end of the biasing member.

15. The method of claim 1, wherein reducing the length of the suture extending between the anchor and the driver shaft is achieved by rotating the driver shaft about a longitudinal axis of the driver shaft.

16. The method of claim 1, further comprising measuring a height of the anchor disposed in the bone so as to ensure the implant is substantially flush with a surrounding bone surface.

17. The method of claim 1, wherein the anchor is inserted into the bone via the driver by rotating the driver coupled with the anchor such that one or more helical threads disposed on an outside surface of the anchor threadably engages with the bone, thereby disposing the anchor at least partially into the bone.

18. The method of claim 1, wherein inserting the anchor into the bone via the driver comprises pressing the anchor into the bone through at least one of forming a pilot hole in the bone or pounding the anchor into the bone.

* * * * *